United States Patent [19]

Hogg et al.

[11] 4,341,471

[45] Jul. 27, 1982

[54] APPARATUS AND METHOD FOR MEASURING THE DISTRIBUTION OF RADIANT ENERGY PRODUCED IN PARTICLE INVESTIGATING SYSTEMS

[75] Inventors: Walter R. Hogg, South Miami; Albert Brunsting, Miramar, both of Fla.

[73] Assignee: Coulter Electronics, Inc., Hialeah, Fla.

[21] Appl. No.: 439

[22] Filed: Jan. 2, 1979

[51] Int. Cl.³ ............................................. G01N 21/53
[52] U.S. Cl. ...................................... 356/343; 250/574
[58] Field of Search ....................... 356/336, 338, 343; 250/574; 350/103, 109, 162, 211, 292, 320

[56] References Cited

U.S. PATENT DOCUMENTS

| | | | |
|---|---|---|---|
| 1,607,084 | 11/1926 | Kenney | 350/286 X |
| 3,481,039 | 12/1969 | Kautz | 350/286 UX |
| 3,508,830 | 4/1970 | Hopkins et al. | 356/338 |
| 3,827,798 | 8/1974 | Alvarez | 350/167 X |
| 4,050,782 | 9/1977 | Ucnida et al. | 350/211 X |

FOREIGN PATENT DOCUMENTS

| | | | |
|---|---|---|---|
| 2701523 | 7/1978 | Fed. Rep. of Germany | 356/343 |
| 170219 | 1/1960 | Sweden | 250/574 |
| 486251 | 1/1976 | U.S.S.R. | 356/338 |

Primary Examiner—John K. Corbin
Assistant Examiner—Matthew W. Koren
Attorney, Agent, or Firm—Silverman, Cass & Singer, Ltd.

[57] ABSTRACT

In an apparatus in which particles are passed through an optical sensing zone to measure their radiant energy distribution such as, for example, light scattering characteristics for the purpose of identifying the particles, means and a method are provided for deviating the collected light in accordance with predetermined different paths to a plurality of different photodetecting devices. The deviation is effected independently of collection by optical radiant energy transmitting or reflecting means. The different photodetecting devices enable the measurement of energy directed along the particular path which is identified with that device. The paths are established by the deviating means rather than permitted to evolve by the scattering phenomena themselves whereby the photodetecting devices can be located in convenient arrangements and may be conventional in construction. Different forms of the invention combine optical reflection or refraction for collecting the scattered radiant energy with optical reflection or refraction for deviation to achieve different advantages and results.

84 Claims, 26 Drawing Figures

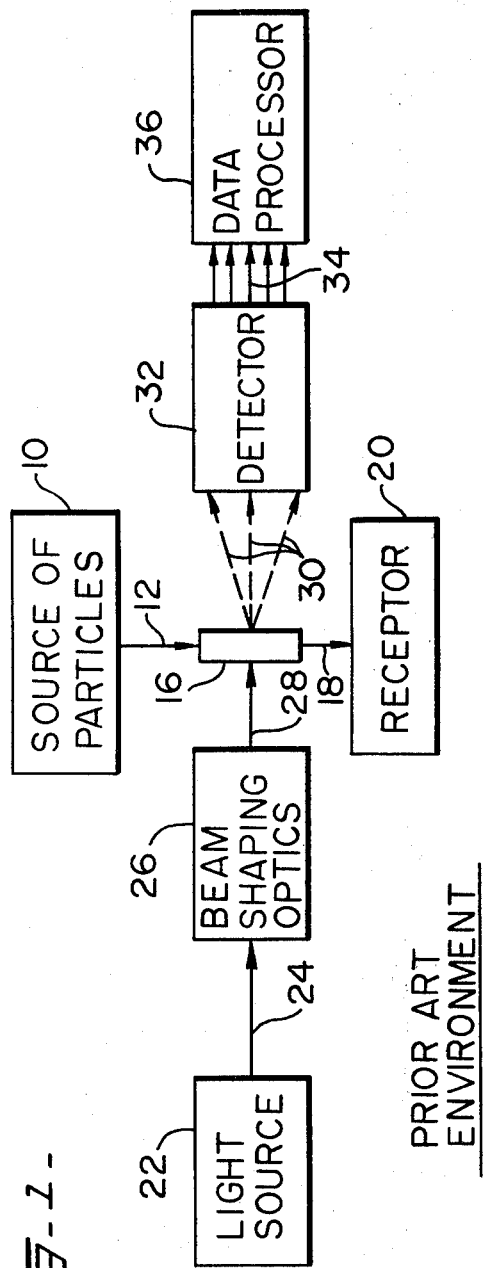

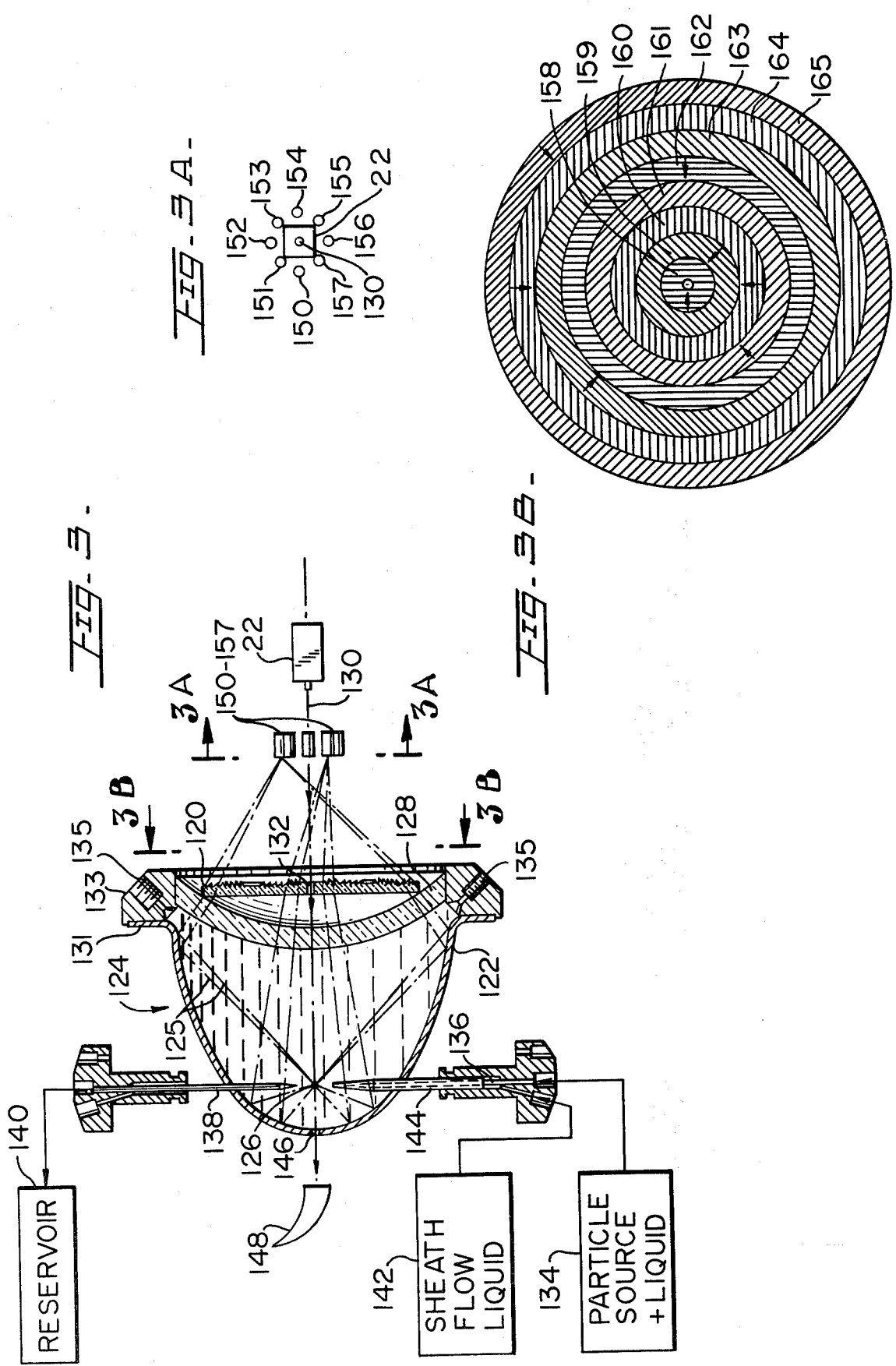

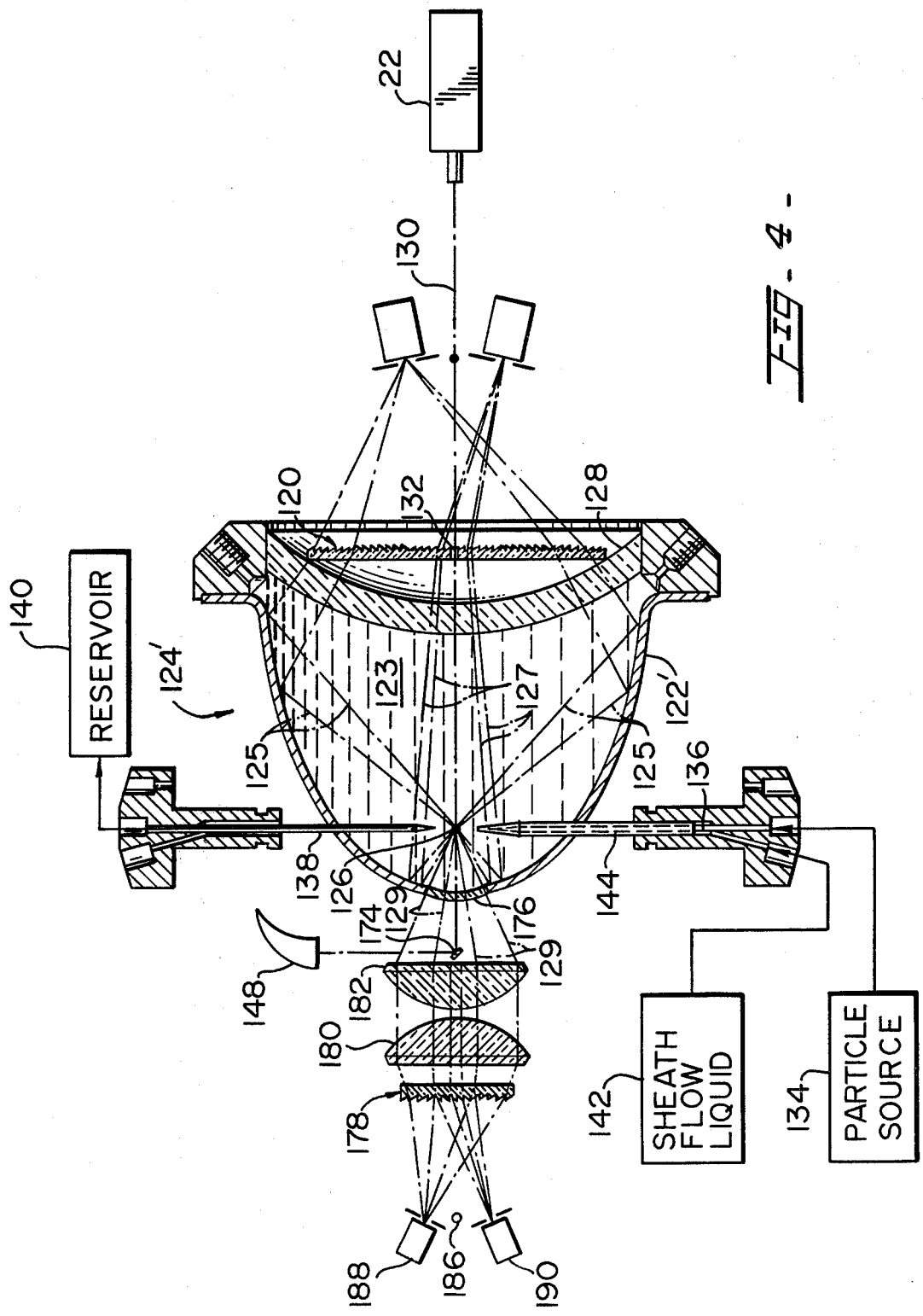

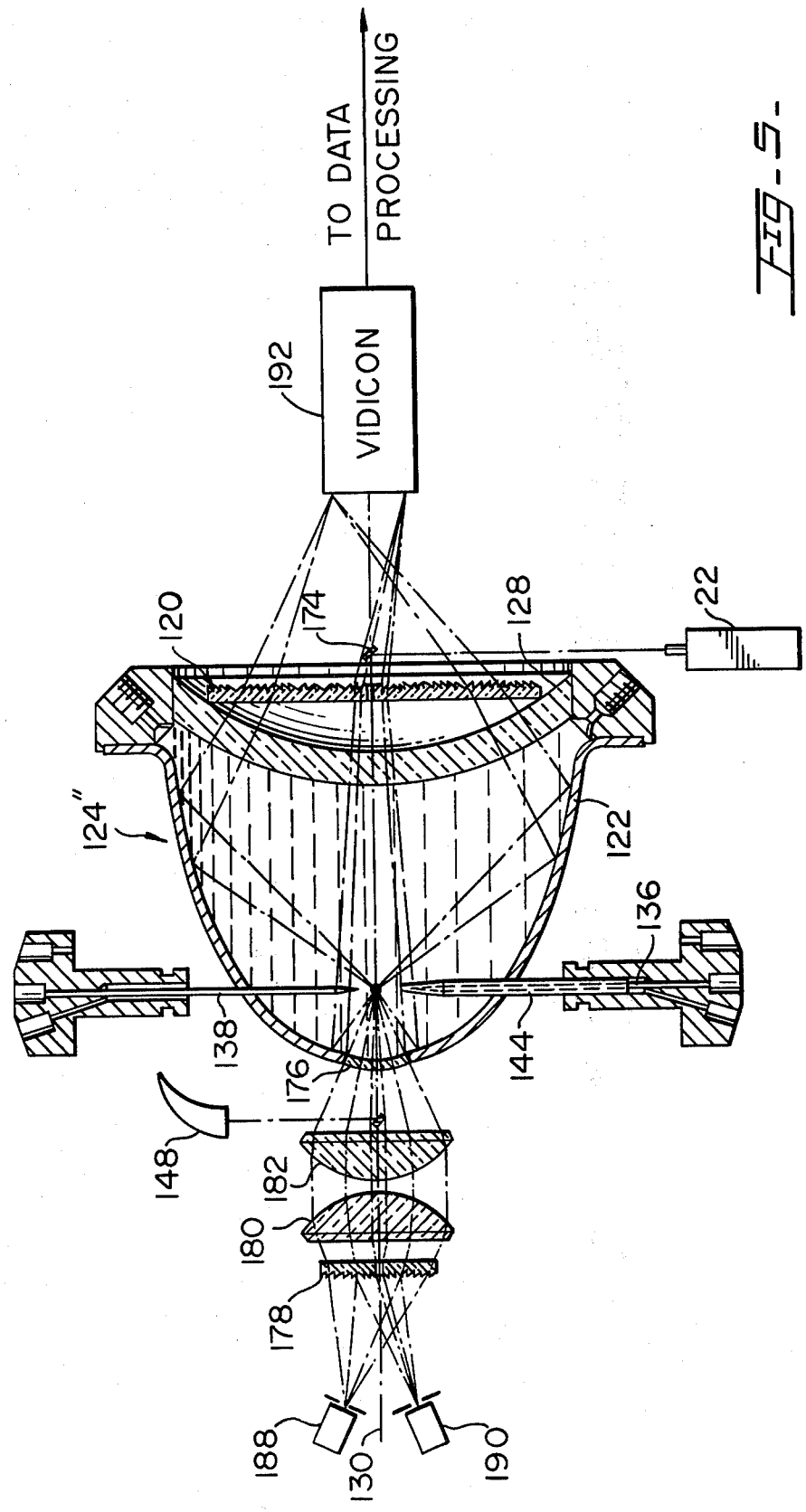

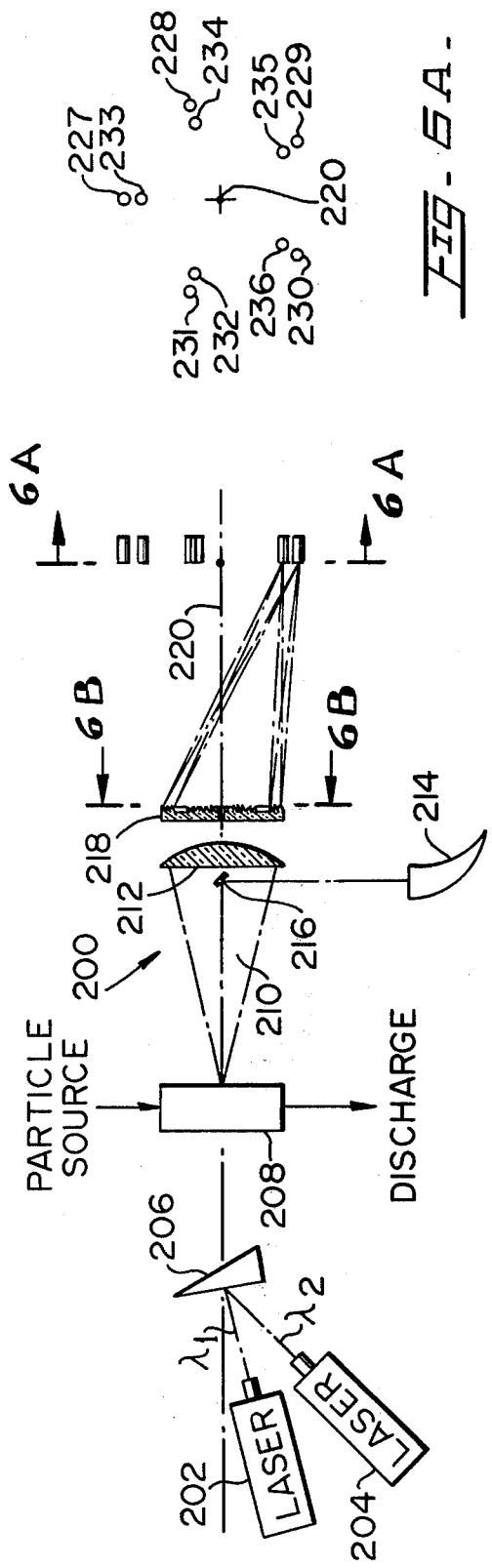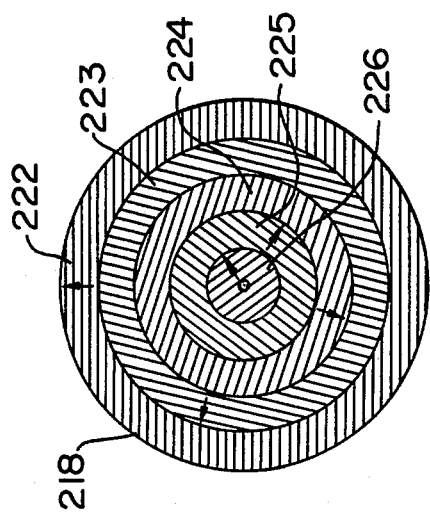

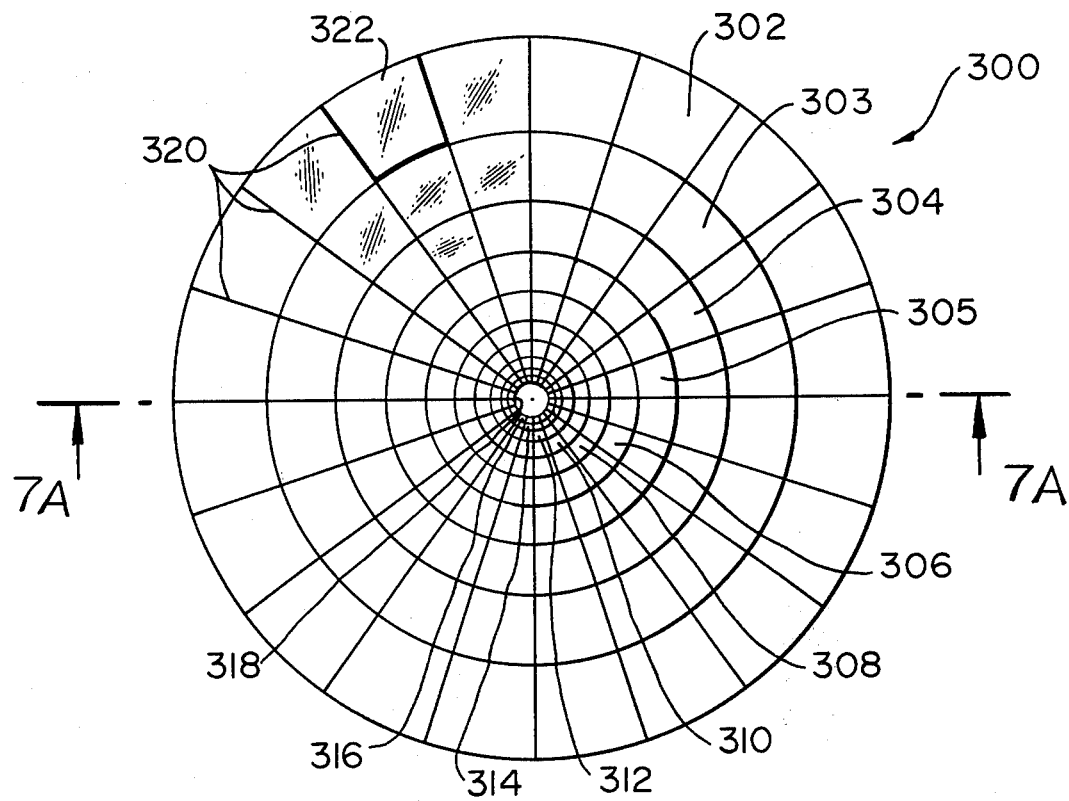
FIG-7-
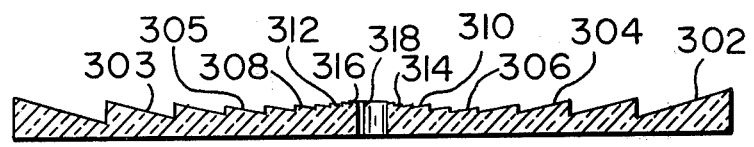
FIG-7A-

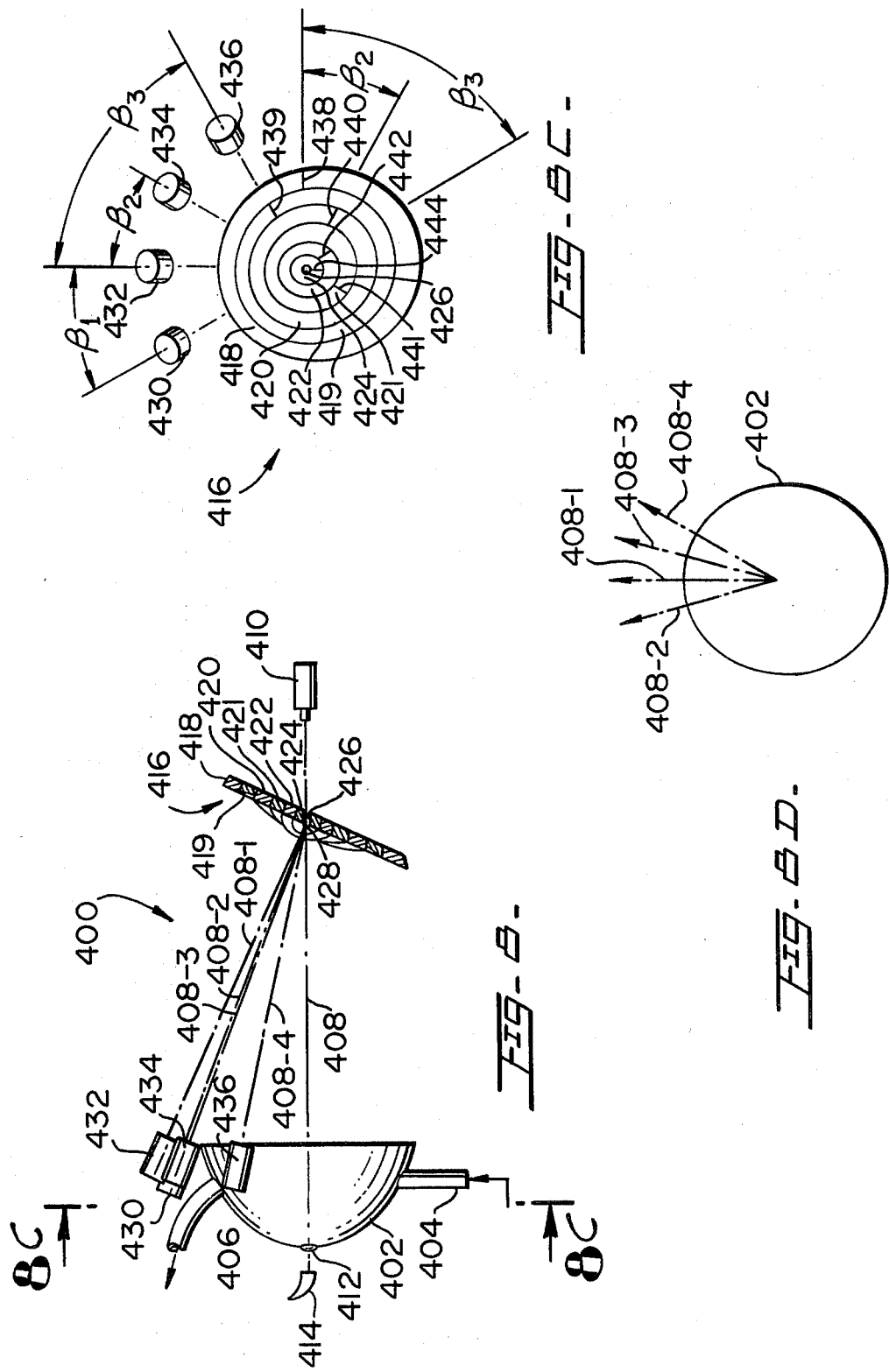

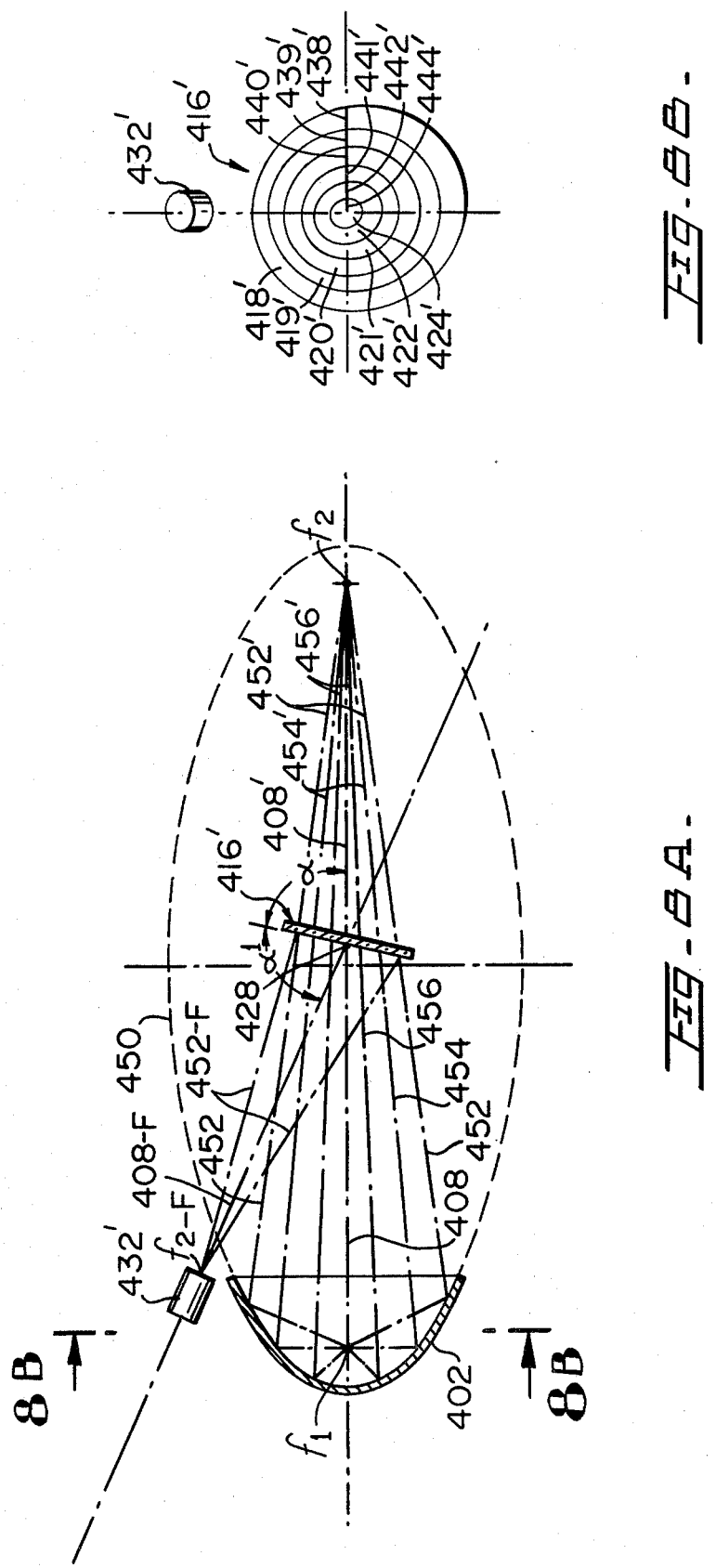

APPARATUS AND METHOD FOR MEASURING THE DISTRIBUTION OF RADIANT ENERGY PRODUCED IN PARTICLE INVESTIGATING SYSTEMS

BACKGROUND OF THE INVENTION

This invention is concerned generally with the measurement of radiant energy distribution such as that of scattered light and more particularly is concerned with the measurement of the energy and direction of light produced and distributed by particles passing through an optical sensing zone whereby to enable the identification of the particles and/or their characteristics. The invention will be discussed in connection with light scattering but is not limited thereto.

The invention herein has relatively wide application but particularly is of value in the identification of white blood cells, cancer cells and other biological particles.

There is a considerable body of literature and prior art on the work which has been done by others in the identification of biological cells and it would be of some value to review the same briefly. It would be advantageous also to delineate the relationship of this invention with the apparatus which has been utilized and is described in the prior art.

Basically, a sensing zone is established in some way by directing a beam of concentrated light to a small volume through which the particles are to be passed, the particles are directed to pass through the zone and the scattered light is detected in different geometric locations around the zone. Scattering may occur backward or forward of the zone relative to the light source.

In its simplest form, a stream of liquid or air carrying the particles is flowed through a pipe and at a transparent location along the pipe a beam of light is projected across the stream. A photodetector on the side of the pipe opposite the source of the beam of light will detect a change in its response each time that a particle passes. Obviously the fact of change enables the particles to be counted. The "shadow" thrown by the particle on the photodetecting device provides some information as to size. Other photodetecting devices can be positioned at locations spaced from the axis of the light beam to give signals which are related to the amount of light scatter in different polar locations.

In biological cells, the condition of the interior of the cell will produce scattering of light in different ways and many of the apparatuses of the prior art are concerned with the method and techniques whereby the effects of light scattering help identify the cells.

Identification of the cells, especially white blood cells, is needed for diagnosis and detection of disease, for the ascertaining of patient condition and the effects of therapy, etc. Present methods and apparatus for this purpose are channeled toward the automation of the identification techniques to enable high speed measurements and positive identification. This is to enable the elimination of the slow, tedious and inaccurate manual methods that have been classically practiced in laboratories, clinics and hospitals.

The systems and apparatus which are known utilize a fluid flow which tends to pass the particles to be measured through a sensing zone one by one. Although the fluid may be a gas, generally in the study of biological particles this is a liquid such as a saline solution whose purpose importantly is to preserve the integrity and the condition of the particles. Gas and air as fluids for transporting particles to and through sensing zones are used more commonly in the study of industrial particles such as fly ash, dust, comminuted minerals etc.

Considering principally biological particles (although the prior art to be mentioned is not necessarily limited thereto) typically such particles are entrained in a sheath of liquid which is either circular or almost planar in cross section at the sensing zone. Several U.S. patents which disclose this type of entrainment and sensing zone are: U.S. Pat. No. Re 29,141; U.S. Pat. Nos. 3,413,464; 3,657,537; 3,705,771; 3,785,735 and 3,791,196.

After the particle passes into the sensing zone, the light or other radiant energy which has been directed at the sensing zone by some means such as a concentrated lamp beam or a laser is measured at different locations relative to the sensing zone. Typical of these devices are several of those mentioned above as well as in U.S. Pat. No. 3,835,315. A system for such measurements is disclosed in U.S. Pat. No. 4,070,113 although the photodetector therein is not described in much detail.

The problem of measuring the scattered light at different locations has been attacked by others but three important disadvantages have been difficult to overcome. The first is the disadvantage of not being able to get enough information because of the difficulty of measuring a plurality of points. The second is the disadvantage of complex and difficult to manufacture apparatus with its attendant companion disadvantage of great expense. The third is the disadvantage of not getting enough energy from the scattered light at all measuring points to give meaningful data.

Each of the four prior art references mentioned hereinafter has one or more of these disadvantages.

The oldest of these references is U.K. Pat. No. 137,637 of 1920 to Pollard which utilizes expensive conical frustums and reflecting prisms. The scattered light is viewed by a microscope and/or measured by crude means compared to those available at the present time.

The second of these references is Frommer U.S. Pat. No. 3,248,551 which utilizes a compound type of annular reflector that has two surfaces and concentrates the scattered light captured by the respective surfaces and reflects same to separate photomultiplier tubes. It is quite obvious from an examination of this patent that the two-surface reflecting device is most difficult and complicated to manufacture; hence one which would require collection from many more than just two angles or polar regions would be even more difficult and expensive to manufacture. In this structure, the collection and deviation of the scattered radiant energy is effected by a single element.

Both the Pollard and the Frommer patents utilize only reflection for concentrating the scattered light thereby not having the simplicity and efficiency of the invention. The number of regions of light scatter from which information can be obtained is severely limited in these prior art devices.

The third and fourth of these references comprise two publications describing a device which is mentioned in Patent 4,070,113 as a type of photovoltaic detector which has concentric rings formed on a disc that is several inches in diameter. The light from the scattering zone is permitted to fall directly onto this detector which then provides electrical signals related to the energy of the light at different distances from the center of the beam. The publications are an article entitled "Light-Scattering Patterns of Isolated Oligodendroglia" by R. A. Meyer, et al. in *The Journal of Histochemistry and Cytochemistry*, Vol. 22, No. 7, pp 594–597, 1974 and a second article entitled "Gynecologic Specimen Analysis by Multiangle Light Scattering in a Flow System" by G. C. Salzman et al. in the same journal, Vol. 24, No. 1, pp 308–314, 1976. In the articles reference is made to the same or a similar detector device which is identified as a Recognition Systems, Inc. detector.

The ring detector which has been described above is quite expensive at the present time. It typically comprises 64 photodiodes arranged in rings and wedges, all on the same substrate. If any element or increment of the detector fails or is damaged it may be necessary to discard the entire device. Additionally, the contacts for the diodes are brought out to a narrow edge segment at which point they are required to be connected into electrical circuitry. This is a delicate and precise operation not easily effected by unskilled technicians.

Additionally the inner rings are very small while the outer rings are quite large. Thus the radiant energy is weakly diffused over the outer rings giving low power density. Detection requires amplification with decrease of signal to noise ratio. Additionally the electrical capacitance of the outer rings is substantially high which results in loading and deterioration of signal. This is a problem where the particles which move through the sensing zone at high speed generate light pulses which may be as short as several microseconds.

The basic difference between the invention and the methods and apparatus which are known lies in the manner in which control of the scattered light is achieved.

The invention herein solves the problems of the prior art to eliminate the disadvantages thereof through the use of several different means. In one preferred form of the invention light deviating means is utilized in the form of a fresnel lens which receives the scattered light from the sensing zone and effects a division of the scattering energy from a large region into increments which represent respective different areas or angles of scatter. This is done by transmitting the scattered light through the lens to achieve independent concentrated beams in an amount equal to the number of elements forming the lens, directing and focussing the resulting independent beams on respective independent photoconductive devices or upon incremental areas of a large photoresponsive device capable of giving independently identifiable signals, for example a television camera element.

In another form of the invention the deviation is effected by a composite mirror having a plurality of elements which respectively reflect radiant energy from different angles to independent photoconductive devices.

The independent photoconductive devices are located in any convenient array, are conventional in construction and hence are highly economical and easily replaced independently. The capacitance to ground is low permitting rapid voltage change and good response thereby preserving the amplitude of electrical signals resulting from the high speed passage of particles. The processing of large numbers of signals is thus rendered easier in relatively simple electronic circuitry than if the signals were not clearly defined.

The invention permits of considerable latitude in configuration, placement, construction and arrangement thereby providing high flexibility for almost any kind of system, but also with no loss in convenience and economy of use.

SUMMARY OF THE INVENTION

Method and apparatus for measuring the distribution of radiant energy produced in particle investigation systems such as light scattering systems.

Particles are directed through a sensing zone which preferably has them passing in such a manner that they traverse it essentially one-by-one. The zone is established by directing a beam of radiant energy such as visible light to the zone and detecting the passage of the particle through the zone by response of a photodetecting device to the disturbance of the normal beam. Optical means are used first to collect and then to cause deviation of the radiant energy beams caused by characteristic scatter from their normal patterns to those which are predetermined by suitable design of the optical means whereby to direct the scatter beams to particular photodetecting devices or photoresponsive areas arranged in a convenient array. Conventional photodetecting devices may be used for this purpose.

The collecting means comprise light reflecting or refracting elements. The deviation-causing optical means comprise light reflecting or refracting elements. Various means and method for enhancing the beams, for making measurements of back-scattering as well as forward-scattering energy; for achieving more information through the use of energy of different wave lengths and for improved convenience and economy of the method and apparatus are disclosed.

BRIEF DESCRIPTION OF THE DRAWINGS

FIG. 1 is a diagrammatic view of the prior art environment in which the invention is utilized;

FIG. 2 is a diagrammatic generally sectional view through a simplified form of the invention showing the manner in which the scattered light from the sensing zone is collected and thereafter deviated to the photoresponsive devices;

FIG. 3 is a diagrammatic generally sectional view through one form of the apparatus of the invention in which an ellipsoidal reflecting device is used to collect the radiant energy and direct it to a fresnelled deviator for deviation;

FIG. 3A is a generally front-on elevational view of the array of photodetecting devices of FIG. 3 taken generally in the direction of the arrows 3A—3A of FIG. 3;

FIG. 3B is a generally front-on elevational view of the fresnelled deviator of FIG. 3 taken in the direction of the arrows 3B—3B;

FIG. 4 is a view similar to that of FIG. 3 but illustrating another form of the invention in which narrow angle forward scattering measurements can be made;

FIG. 5 is another view similar to that of FIG. 4 but illustrating the use of a television camera tube as a photodetecting device in place of conventional photocells;

FIG. 6 is a diagrammatic view of a system utilizing the invention in which the beam of radiant energy is formed of at least two sources of light of different wavelengths;

FIG. 6A is a front-on elevational view of the array of photodetecting devices of FIG. 6 taken generally in the direction of the arrows of FIG. 6;

FIG. 6B is a front-on elevational view of the fresnelled deviator assembly of FIG. 6 taken generally in the direction of the arrows 6B—6B of FIG. 6;

FIG. 7 is a view similar to that of FIG. 6 but showing a modified form of the invention utilizing a plurality of wedges instead of fresnel prisms, all assembled as shown;

FIG. 7A is a sectional view through the same along the line 7A—7A and in the indicated direction;

FIG. 8 is a diagrammatic view of another system utilizing the invention in which the scattered radiant energy is collected by a reflector of ellipsoidal configuration and deviated by a special composite reflector assembly;

FIGS. 8A, 8B, 8C and 8D are diagrams used to explain the operation and construction of the system of FIG. 8.

DESCRIPTION OF THE PREFERRED EMBODIMENTS

Figure 2A:
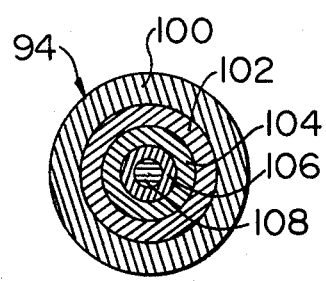
FIG. 2A is a front-on elevational view of the fresnelled deviator assembly of FIG. 2 showing one form thereof and FIG. 2B is the same but showing another form thereof.

According to the invention, the method comprises providing a sensing zone and passing particles through this sensing zone to sense their presence and to direct radiant energy thereon. The particle scatters the radiant energy and this scattered radiant energy is collected by suitable optical means and focussed or confluenced towards a point in space, but it is intercepted by an assembly of elements which causes the energy in the different angles or paths or geometric parts to be deviated from the convenience of measuring them. The measurement is effected by an array of photodetecting devices or elements which respond respectively to the intensity of energy present in the particular angle, path or part. This array may be a television vidicon surface. From this data, by reason of information which is known from previous studies, one can identify and/or determine the character of the particle which produced the scattering.

The invention is believed to provide a greater quantity and more accurate scattering data than known methods and apparatus as a result of which it is useful for the establishment of information related to specific types of particles by passing known particles into the sensing zone in order to learn the scattering effects of such particles for use in other work where unknown particles are being identified.

In a specific sense, the scattered energy can be thought of as hollow or solid cones of light or radiant energy each of which is brought to a focus at the location of the photoresponsive device or element which is intended to make the measurement for that specific cone. The scattered energy can also be measured as part cones for additional information, as for example when the energy may not be in symmetrical geometric form, although this is unusual.

The novelty of the invention lies principally in forming a lens or a mirror out of a plurality of optical elements, usually annular in form, which "point" or are focussed in specific directions to enable the energy deviated thereby to be confluenced and measured. The elements may be assembled in a single integrated member such as a linear fresnel lens whereby the practical thickness of the resulting equivalent prismatic element is much less than it would be if actual prisms were used. In the case of a lens, the same is normally formed of generally annular prism elements but could be synthesized from a plurality of small prisms assembled to provide a lens which can produce a large number of beams to be directed onto the incremental elements of a television camera tube for measurement. This could be done as well for a mirror whose elements are rings or arcuate parts of rings assembled together.

FIG. 1 illustrates a prior art system which shows the environment in which the invention is utilized. Here a source of particles 10 is provided which may feed, for example, white blood cells, exfoliated cells or the like in a diluent by way of the path 12 to the flow-through element 16. This may be effected in this simple flow or with some additional second diluent which produces a particular form of geometric cross section of fluid in a sensing zone. The additional diluent may comprise a stream of liquid under pressure surrounding the main flow to produce sheath flow conditions through the body of the liquid whereby to confine the particle stream. The basic stream itself may form a flat planar stream through the sensing zone.

From the flow-through element 16, the fluid that has been passed through moves along the path 18 to a suitable receptor 20 which may be waste, another system or an accumulator.

The source of radiant energy is here shown as a laser 22 but can be any suitable source of light or the like. The invention provides an efficiency which enables the laser used to be of low power with a minimum of heat generation. The resulting beam is passed along the optical axis 24 to an optical system or train represented by the lens 26 which shapes and focusses the incident radiant energy onto the sensing zone of the flow-through element 16, the emergent light being scattered and providing a plurality of radiating beams indicated at 30. Only three such beams are shown as representative, there being a continuous spread of the energy, the amount of radiant energy at any diverging angle and in any sector being dependent upon the size, shape, orientation and morphology of the scatterer (particle) plus characteristics of the incident light. A detector 32 is provided which is ideally constructed to respond differently at its different geometric aspects facing the beams 30 so that at incremental locations over the area of its frontal aspect it will produce different identifiable signals, notably, signals of different intensities. These signals are passed through the channels 34 to some form of data processor 36. From the signals and their relationship to one another, both as to intensity and geometric location, the particle which produced the signals may be identified or at least characterized.

The detector 32 of the prior art has several optical disadvantages which are overcome in whole or in part by the invention described herein. The detector 32 has a large number of photoresponsive elements in its array because it was designed for many types of distributions of radiant energy. However in particle investigating systems, different populations of particles have different, optimal detection areas for the photoresponsive elements in general. By using different radiation redirecting means, such as the fresnel refracting device of this invention, the different optimal detection areas are easily and inexpensively obtained.

Although a large percentage of the radiant power scattered by a particle proceeds in the near-forward direction, the information carried by the scattered light is contained throughout the $4\pi$ steradians total solid angle centered at the particle. It is information which is sought; power per se is useful only as it increases signal-to-noise ratio. Using the detector 32 without optical elements between it and the particle, appreciably less than half of the total radiant information can be made to fall on the detector. By using the reflector of the invention, most of the total solid angle is available, and it may be easily subdivided into regions for optimal collection of information.

One could say that the combined radiant energy deviating means and array of photodetectors of the invention is the element identified as 32 in FIG. 1.

In FIG. 2 there is illustrated one of the simplest forms of the invention. The point 40 represents the location of what may be termed the scattering point, this being, for example, a sensing zone through which particles are flowed. Although not here illustrated it may be assumed that these particles enter the sensing zone laterally of the optical axis 42 and cross the axis at said point 40 one at a time. Light or other radiant energy is directed from the left in the view toward the scattering point 40 along the optical axis 42 with the central or main portion of the beam being captured by an axially located angled mirror 44 directing the central portion of the beam to a laterally located absorbing device 46 which is shown in the art as a light dump.

The scattered rays of radiant energy from the scattering point 40 are concentrated or collected by a lens 90 which for convenience is in fresnel form. It should be understood that any optical or lens system could be used for the same purpose, that is, the prevention of the spreading of the scattered rays 48 and concentrating them towards a point such as for example, the point 92.

The distances from the scattering point 40 to the lens 90 and from the lens 90 to the point 92 are equal and will determine whether there is any "magnification" of the scattered light by the lens 90 or an equivalent optical system. If the distances are both equal to twice the focal length of the lens 90, magnification will be unity, but this can be adjusted to other values if desired. Immediately following the lens 90 to the right as viewed in FIG. 3 there is an element 94 which is an optical assembly whose construction and function will be described.

The function of the element 94 is to capture radiant energy from a specifically defined geometric frontal area of the combined scattered beams 48 and to deviate the same as the energy or light passes through a particular portion of the element 94 from rear to front so that the radiant energy collected by the lens 90 will not tend to be directed to the focal point 92 as physically demanded by the action of the lens 90, but instead will be redirected to a point laterally of the axis 92. As indicated in FIG. 2, one set of transmitted rays 50 which may be assumed to have a hollow conical configuration is shown being deviated to and confluenced upon a photodetector 96 while a second set of transmitted rays 52 of the same general configuration is shown being deviated to and confluenced upon a photodetector 98. These photodetectors are only exemplary of a plurality which together receive many sets of rays, but each detector receiving only rays from a specific geometric portion of the scattered radiation. Their placement is at locations which will be convenient and can be widespread so that there is a practical distance between them. The location is controlled by the angle of deviation of the transmitted rays and the distance from the lens 90.

An advantage of this arrangement is that the photodetectors can be standard photocells which are readily available. The radiant energy from the different portions of the element 94 is confluenced on these photocells which may now be quite small and hence provide a better signal-to-noise ratio, lower capacitance in the circuits used and reduced costs. Replacement of defective or damaged photocells is readily effected without discarding a substantial and expensive part of the apparatus.

Only two sets of rays 50 and 52 are shown in FIG. 2 along with their companion photodetectors 96 and 98 but it should be understood that there will be a separate set of rays and an individual additional photodetector for each predetermined segment or frontal geometric area of the element 94.

In FIG. 2A there is illustrated one form of the element 94 in which the element is made out of a series of annular fresnelled prisms 100, 102, 104, 106 and 108. The number of prisms here shown is five for convenience, but any suitable other number could be used. It is understood that their respective analogs are five conventional prisms. The ridges due to the sawtooth cross sections of the various parts are indicated by cross hatching. Radiant energy is deviated by an angle which depends upon the slope of the ridge surfaces and in directions perpendicular respectively to these ridges. The solid angles of radiant energy captured in this case will form in effect five conical composite beams of which the beams 50 and 52 comprise those provided by the outer two annular prisms 100 and 102, respectively. Generally for the identification and study of biological particles the prismatic elements of the assembly 94 will be symmetrical about the center of the element 94. There will be a separate photodetector for each set of beams or solid angle geometric portion of the total radiant energy.

Figure 2B:
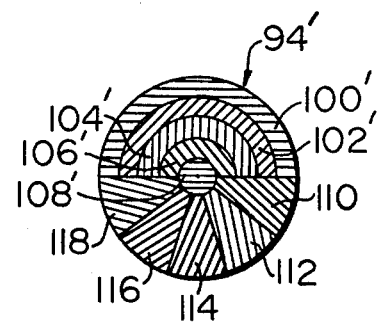

In FIG. 2B an arrangement of elements composing the assembly 94' is illustrated in which the upper half of the element 94' is made out of annular fresnel prisms similar to those of FIG. 2A but only half of each annular prism element is used. Using only half is usually acceptable because of the normally symmetrical configuration of scatter patterns. Thus, there are four such semi-annular prismatic elements 100', 102', 104' and 106'. The center element 108' may be cylindrical for convenience of construction. In addition there are wedge shaped prismatic elements 110, 112, 114, 116 and 118 which collect and concentrate or confluence rays of the scattered radiant energy of a different geometric area than annular. In this case the wedge shaped prismatic elements may be used to identify the presence of elongate constituents in certain particles. There will be a separate photodetector for each of the wedge shaped prismatic elements 110 to 118.

In the use of the apparatus, the electrical signals from the photodetectors 96 and 98 as well as all of the others which are not illustrated will be channeled to a suitable electrical system where the data will be processed. The analog signals may first be converted into digital if needed for the processing. For example, a computer may have a series of characteristics identified in its memory against which the signals are compared to ascertain the identification of the particle which caused the scattering. Scattering could have been caused by different kinds of structures and/or constituents within the particle, as for example, the organelles and their different densities, configurations and numbers.

Attention is now invited to the composition of the element 94 in FIG. 2. As seen from FIG. 2A the assembly is formed of five annular parts 100 to 108 each of which is prismatic in form although annular. Each annulus has the same prismatic cross sectional angles as though formed from the same prism but with different diameters.

This element 94 is made out of some suitable material which will refract the particular wavelength of radiant energy being scattered. It can be glass or some form of synthetic resin, which as explained below, can be molded readily. It is thus dielectric normally and can be described as such. What follows is an explanation of the construction and operation of element 94.

It is only necessary to have the two faces of the element 94 where the rays of radiant energy enter and exit in the form of two planes which are at an angle to each other. The direction of any ray or assembly of rays entering the dielectric material of the element 94 will be rotated about an axis which is parallel to the intersection of these two planes. The distance the ray travels in the dielectric material per se is immaterial; hence, in the circumstance that optical resolution is of secondary importance, it makes no difference whether the front and rear surfaces of the element 94 consist of two single planes or whether one or both are broken up into many small planes all having the same angle with respect to its opposite face. This is the principle which makes fresnel prisms and lenses practical and which enables them to be made lightweight and thin.

One direct way to make the element 94 is to take a large fresnel prism and cut as by sawing along concentric circles to divide it into a set of annuli. Once cut, the annuli are all rotated with respect to one another so that the ridges of the fresnel lens are at different angles with respect to some reference and cemented together in a disc with suitable cement. This is illustrated in FIG. 2 where the annular parts are 100, 102, 104, 106 and 108. The cross hatching is only intended to show different directions of prismatic ridges.

This procedure readily produces a useful device, albeit somewhat expensive because of the labor involved. A problem with this technique is that when high resolution is needed or if, as frequently desired, the radial thickness of inner annuli become progressively smaller, the procedure becomes difficult because of the finite size of the tools which are required. Further, the orientation and adjustment of the individual annuli are delicate procedures.

Figure 2C:
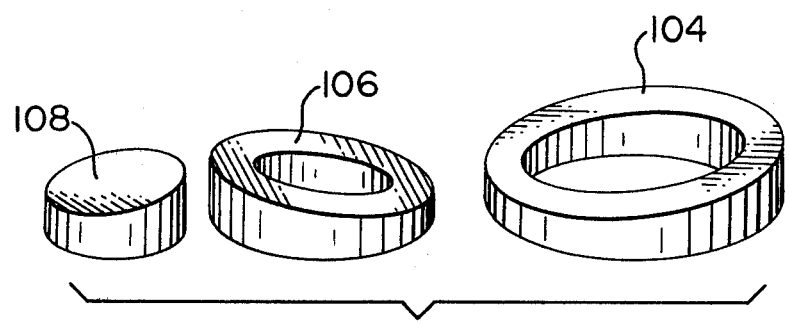
FIG. 2C is a perspective view of several cylinders which can be assembled to produce a master for making a deviator of the type shown in FIG. 2.

When the radial thicknesses of the annuli approach the dimensions of the linear pattern of a commercially available fresnel prism, it becomes practical and equally effective to form the element 94 from simple two-plane prisms. Thus an alternative exists between making cylinders from a simple prism or making prisms from simple cylinders. Obviously, the latter procedure is preferable. It is merely necessary to form an inner cylinder and as many pieces of tubing as the number of annuli needed out of the proper dielectric material such as glass or quartz. The pieces of tubing are assembled concentrically and secured to one another by a temporary cement such as wax, a short axial section piece cut off, polished and lapped to the desired prismatic angle. After polishing, the wax may be melted out and the rings as shown at 104, 106 and 108 in FIG. 2C are rotated with respect to each other as desired and reassembled with suitable cement. This small assembly would typically be substituted for the inner parts 108, 106 and 104 of FIG. 2A if it is desired to have high resolution for the low angle scatter.

The above techniques are useful in producing individual or experimental devices 94 according to the invention. When building them in production quantities, once it has been determined what angles are to be observed by each of the several photocells 96, 98 etc, a master may be made of any suitable material. This may then be used to make inexpensive duplicates using known techniques such as disclosed in Alvarez U.S. Pat. No. 3,827,798. The elements 94 can be molded in production. It is feasible to make the master from which the mold for element 94 is formed out of non-optical material such as brass or steel and assemble its parts by brazing or welding. The dimensions and angles would have to be precisely computed and the parts cut on machinery that is responsive to computer data or tape.

Once the fresnelled element like 94 has been made for a given apparatus, the distance from the scattering point 40 to the element 94 must be the same in all duplicates of the apparatus. Likewise the placement of the photoresponsive devices 96 and 98 and all others that may be used therewith must be the same as the respective positions for which the optical element 94 was designed. Rather than being a disadvantage, this enables the apparatus to be built using tools, dies, jigs and fixtures which enable assembly line production methods.

It is feasible to combine the lenses 90 and prismatic element 94 into one integral unit and/or mounting.

Figure 2D:
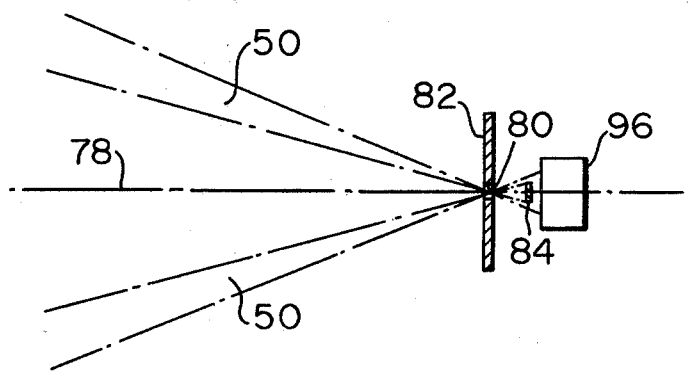
FIGS. 2D and 2E are diagrammatic generally sectional views of a structure used in apparatus such as shown in FIG. 2 to enhance the operation thereof by purifying the beam of radiant energy reaching the photodetector.

In FIG. 2D there is illustrated a portion of the structure of FIG. 2 but enlarged and modified to show the effect of an arrangement which includes an iris. The scattered beams of light, scattering point and other parts of FIG. 2 are not shown for clarity. The transmitted cone of radiant energy or beam 50 is here shown emerging from the annular element 100 on an optical axis 78 (which is not shown in FIG. 2) in alignment with the photodetector 96. Where the angles of the optical axes of the respective parts of the beam such as 50, 52 and the others are disparate, it is likely that the photodetector elements will be arranged perfectly normal to the said optical axes, respectively, rather than normal to the optical axis 42 in FIG. 2. The latter is only for illustration.

The cone of radiant energy represented by the beam 50 is substantially symmetrical around the axis 78. This cone is focussed on the central aperture 80 of an iris 82 instead of on the surface of the photodetector 96. This latter may include a photocell element or the element of a photomultiplier or the like where the focus normally takes place. The photodetector 96, as seen, is behind the iris 82 with respect to the source of the beam 50. This arrangement prevents any radiant energy from reaching the photoresponsive device 96 except that which is being transmitted from the sensing zone 40 be means of the annular prismatic element 100. The center of the photocell may be sensitive to the extraneous light, say from the other parts of the fresnelled element 94 and from light which concentrates on the axis 42 after passing through the element 94 while getting past the mirror 44. This center may be blocked off by a centrally located mask 84 as shown.

Figure 2E:
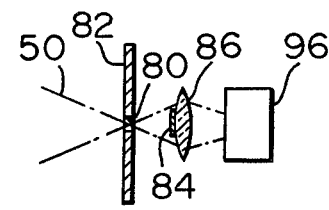

In FIG. 2E there is another arrangement which, in addition to the iris 82 and its aperture 80, there is a small lens 86 between the aperture 80 and the front surface of the photocell 96. The mask 84 is then easily located on the central surface of the lens. This lens could be part of an integral array of plastic lenses serving all of the photoresponsive devices and suitably selectively masked by paint to provide the individual iris effect. The result would be to increase the signal to noise ratio of the photocells or other photoresponsive devices.

Referring once more to FIG. 2C, as mentioned above, the circular components of the element 94 are based upon the concept that the components have been individually formed out of cylinders. Actually, in making the master, such cylinders conveniently can be cut from a single flat prism and reassembled with different orientations. The thicker portions will be located around the exterior of the assembly 94 and the inner ones will be increasingly thinner with the result that each component will receive the scattered rays from an annular area and deviate the same to a focus spaced from the axis in a direction different from all others. Orienting the prisms so that they face in directions equally spaced around the axis 42 will place the foci equally distant around the axis as well. They may be located slightly spaced from one another along the axis, but this presents no problem in the manufacture of the element 94 as a fresnelled element. Nor does it produce any problem with respect to the location of the individual photoresponsive devices. The distance from the axis 42 will depend upon the original angle of deviation of the prism from which the parts are developed.

It is to be understood that the elements 94 will be an integral molded member in production, the above-described master being used to build such mold.

In FIG. 3 there is illustrated a form of the invention which utilizes, in addition to a fresnelled element 120 an ellipsoidal reflector 122. The apparatus is generally designated by the reference numeral 124. The sensing zone 126 in this case is located in the interior of the reflector 122 which, as will be explained, is filled with diluent 123 of the same index of refraction as that which carries the particles.

The advantage of the addition of an ellipsoidal reflector as used here is that since the reflector 122 surrounds the sensing zone 126, it can capture the scattered light for a polar scattering angle which occurs in the vicinity of 0° to, say 135°, depending on the eccentricity of the ellipse as well as in all azimuthal angles. (In FIG. 3 the polar angles lie in the plane of the paper and the azimuthal angles lie in a plane perpendicular to the paper.) Back scattered light becomes increasingly important as the size of the particles to be measured decreases. For example, white cells and other biological cells may be of the order of 10 to 15 microns in diameter and their internal structure will normally be that which gives rise to the wider angles of scattering may have radii of curvature of the order of one micron and less.

In FIG. 3 the ellipsoidal reflector 122 has its forward opening closed off by a spherical transparent closure 128 that does not affect the direction of the collected radiant energy as it leaves the reflector 122. This closure has as its center of curvature the right hand focus of the ellipsoid. Radiant energy originating in the laser 22 passes along the axis 130 through an opening 132 in the element 120 to the sensing zone or scattering point 126. The particle source 134 pumps the particles in the diluent liquid into a central conduit 136 into the interior of the ellipsoid 122 where it passes through the sensing zone 126 and into the discharge pipe 138 to a suitable reservoir 140 outside of the ellipsoid. In the meantime a second source of liquid 142 injects diluent through the concentric pipe 144 surrounding the conduit 136 so that there is a sheath flow confining the particles to the sensing zone 126.

The laser beam passes through the sensing zone 126, out through a transparent light port 146 in the rear of the ellipsoid and to a light beam dump 148 outside of the ellipsoid (Theoretically the spherical closure 128 should be perfectly flat where the laser beam passes through to prevent spread, or alternatively beam shaping optics may be used. The effect on the laser beam, however, will normally be so small in most cases that it can be ignored.)

Forward scattered and back scattered light is directed to the fresnelled element 120 and deviated in the manner which has been described to an array of photo-responsive devices 150 to 157 that are arranged in a circle around the axis 130. In this case only several are shown in the side view of FIG. 3 but it is intended by way of example that there be eight such photocells arranged as illustrated in FIG. 3A. This results from the establishment of eight circular zones in the surface of the element 120 providing eight different annular prisms as shown in FIG. 3B. These are designated 158 to 165, each being of a different polar orientation to divert a different ring of forward scattered and back scattered light to one of the respective photoelectric cells 150 to 157.

In this case as in others described, the angle of deviation of the basic prism determines the radius of the ring defined by the proper placement of the photodetectors at points of beam focus.

The construction of the apparatus 124 which is illustrated is not intended as limiting. In FIG. 3 the ellipsoidal reflector 122 has a rim flange 131 to which is attached a bezel 133. The bezel carries the spherical transparent closure 128 and the fresnel element 132. The plugged openings 135 enable drainage and bubble removal.

In FIG. 3B there is a frontal view of the element 120 with the individual annular prisms cross hatched to show their orientation relative to the axis. Arrows indicate the direction towards which the transmission of the radiant energy impinging on the rear surfaces thereof will be deviated. As seen, the arrows are at equal angles relative to one another so that the array of photoresponsive devices 150 to 157 can be arranged at equal angles about the axis 130.

The apparatus 124 of FIG. 3 utilizes as its principal feature the fresnelled element 120 whose construction and operation do not differ materially from the construction and operation of the element 94. In addition to the use of the fresnelled radiant energy transmitting element in apparatus 124 there is a reflecting element comprising the ellipsoidal reflector 122 which collects the forward scattered radiant energy as well as back scattered energy, the latter being collected from much wider angles than would be achieved without the use of the ellipsoidal reflector 122.

Looking for the moment at the apparatus of FIG. 2, it should be appreciated that the laser being on the left and the light collecting occurring on the right, the only radiant energy being measured is that of the forward scattered light. In the case of the apparatus 124 of FIG. 3, the laser 22 is on the right, the radiant energy which is represented by the beams 125 being typical of the back scattered light and being directed to one of the photocells. The radiant energy which is represented by the beams 127 reflecting from the portion of the ellipsoid 122 to the left of the sensing zone 126 is typical of the forward scattered light and is directed to another of the photocells.

The apparatus 124 of FIG. 3 will give more data and information than the apparatus of FIG. 2 because its radiant energy gathering characteristic is more efficient, using transmission of the light for deviation to predetermined locations and in addition, gathering the radiant energy through the use of an efficient reflector.

In connection with the structure 124 of FIG. 3, it would be practical to have an ellipsoidal surface as shown which will capture all scattered light from about half a degree to 140°. The light is directed by the interior of the ellipsoid, that is, the left hand end as viewed in the figure, to the right hand focal point. The interposed fresnel element 120 is shown to the left of the second focus in the view, but there could be a negative lens before the second focus or suitable positive lenses after the second focus to reduce the collection angle of the fresnel element 120 and any or all of the photocells to adjust for optimum collection results. The lens would be small and have a very small focal length, but will thus be economical.

The structure of FIG. 3 may have several practical disadvantages. The radial thicknesses or widths of the zones 158 to 165, if designed to subtend equal angles as viewed from the sensing zone become so small closer to the center of the element 120 that fabrication may present problems. Another disadvantage is that commercially available ellipsoidal mirrors generally have an access hole at the closed end which is quite large.

According to the invention, in the device which is illustrated in FIG. 4, these problems to a large extent solve one another.

In FIG. 4 there is illustrated a system 124' which takes advantage of the large opening in the commercially available ellipsoidal reflectors for collecting forward scattered light. The reference characters are generally the same as in FIG. 3. The ellipsoid 122' has the same means for forming the sensing zone and the same type of fresnelled element 120. The light dump 148 is off to one side of the axis 130 and the center beam is directed there by a small reflector 174. The ellipsoid is drawn approximately full size. The ellipsoid 122' has the typical large hole 176 which is covered by a transparent spherical window centered on the sensing zone that will not adversely affect the operation of the device.

By using the hole 176 as a window, the collected light is split into two parts, each of which is subdivided in accordance with the teachings of the invention by suitable fresnelled prism elements. The element 120 will subdivide the back scattered light while the fresnelled element 178 will subdivide forward scattered light which passes through the hole 176, this being generally the light that would normally have to be handled by the innermost rings of the element 120. Such light produces the beams 127 and the beams 129, for example. This forward scattered light 129 is collected and concentrated by the lenses 180 and 182 which are arranged in a classical assembly.

The lenses 180 and 182 focus the light at a point 186 along the axis 130 but before the light beams can converge to any great extent they are captured by the element 178 and their various parts deviated and focussed or confluenced on a series of photodetectors, two of which are shown at 188 and 190. Obviously, there will be a complete array of these around the axis 190 to the extent that is required by the parameters of the particles being studied.

This arrangement permits the light which would otherwise be reflected at the smaller inner angles of the ellipsoid 122' to be magnified and makes it unnecessary to have extremely small rings on the fresnelled element 120 with corresponding small radial widths for such rings. It also leaves room on the optical axis for mirror 174 and beam shaping optics (not shown). Incidentally, all versions of the invention may have some form of beam shaping optics included.

In coordinating and collating the data from the photodetectors, it is preferred that the data be processed in a computer. The rings for the elements 120 and the other fresnelled elements of the drawings preferably subtend equal angles as viewed from the sensing zone, especially since the rings of a circular diffraction pattern are so spaced, but the computer may be programmed to compensate for rings of any varying width in the data being gathered. In FIG. 4 the rays of light which are shown are for an element 120 intended to have each of the rings take care of 11.25° increment windows.

It is noted that the intensity of the back scattered light which is achieved by the apparatus 124' of FIG. 4 is normally substantially less than that of the forward scattered light. Instead of photodetectors of the conventional type, photomultipliers could be used with advantage although this will increase the overall cost of the apparatus. The number of such photomultipliers needed for good resolution is another important factor in cost. The utilization of the economical elements 120 and 178 provides advantages over known detecting systems, even with the use of expensive photomultipliers.

In the structure of FIG. 5, everything is substantially the same as that of FIG. 4 with one important difference. Instead of an array of separate photoresponsive devices, a single television camera element or tube 192 is utilized. The reference characters used in this view are generally the same as in FIG. 4. The apparatus itself is designated 124". When a particle goes through the sensing zone, scattered light from each cone is focussed by the element 120 onto a discrete zone or increment of the target of the television camera element. When the particle has passed through the sensing zone, which time may be sensed by detecting the trailing edge of one of the pulses from the forward scattered light, the array of charges on the target of the television camera tube can be scanned and transmitted to the computer.

The relatively intense forward scattered light can be directed to simple photocells 188 and 190, by photomultipliers or by another television camera tube.

It is clear that since the resolution of television camera tube target is much greater than that of ordinary photodetectors, the amount of information which can be obtained from any particle can be quite substantial, being limited only by the resolution capabilities of the fresnelled elements such as 120.

If the fresnelled prism element such as 120 is made out of parts or increments from the same prism, all focal points or spots of light will appear in a circle whose radius is the distance from the fresnelled element to the receptor (the camera tube target or the surface of the photocell) multiplied by the tangent of the deviating angle of the original prism.

By using parts from prisms having different deviating angles, several rings of light spots (focussed light) of different radii can be formed. Thus, the area occupied by the array of spots can be compressed for the purpose of concentrating all spots on a television camera tube target. The number of rings of spots will be the same as the number of different prisms used to form annuli.

In FIG. 6 there is illustrated an apparatus 200 in which several rings of spots (as indicated in FIG. 8A) can be achieved through the use of radiant energy of different wave lengths. Thus, there are two lasers 202 and 204 directing beams of different wave length light through a prism 206 which combines the beams and sends them both through a flow chamber of element 208 which has a sensing zone. The scattered light 210 is collected by the lens 212, the central energy being dumped at 214 by way of the central reflector 216. The light passing through the lens is now captured and deviated by the fresnelled prism element 218 but because there is radiant energy at two different wave lengths, the deviation will be different for each, and each color of light will be focussed at a different spacing from the axis 220. The number of spots will be twice the number of component prism rings of the element 218. The refraction will be different on any dielectric material for different wave lengths.

Thus, in FIG. 6B it is intended that the element 218 have five rings 222-226. Since this will produce an array of ten light spots, as shown in FIG. 8A there will have to be ten photocells 227 to 231 receive the confluenced light of one wave length from the five rings 222 to 226 and the photocells 232 to 236 receive the confluenced light from the same respective rings but of the other wave length. The two rings of photocells will be in slightly different planes due to chromatic aberration of lens 212.

This type of information is readily processed by computers and is quite valuable for cell identification. Inasmuch as the size, shape and orientation of constituents information from any particle which passes through the sensing zone is detected by all of the photocells and is common to both scatter patterns of different wave length, any differences between these patterns which can be measured is due to the change in refractive index of the different parts of the particle from one wave length to the other. The change of refractive index relative to wavelength is different for different materials. Since particle information which has been stored can include such data it is obvious that this increases the usefulness of the apparatus and the positiveness of identification of the particle.

The construction of the so-called fresnel element of the invention which is identified as 94 in FIG. 2, 120 in FIG. 3 and in FIG. 4, 178 in FIG. 4, 120 and 178 in FIG. 5 and 218 in FIG. 6 in practically all cases will be effected by the use of molding techniques where a master is made first out of glass or quartz, properly ground and polished and with the various components properly oriented. As mentioned, even non-optical materials may be used. In the making of the master the actual cutting of the annular rings from a single prism is practical for larger rings. Where the inner rings get smaller and smaller this becomes more difficult; however, it is feasible to have telescoping glass or quartz tubes of proper wall thickness ground off and polished at the proper prismatic angles and assembling these with larger cut rings to form an assembly for the master. The tubes would be held together by some cement such as wax while the proper angle is cut across all of them after which they would be released from the adhesive to orient them properly and re-fixed in such orientation.

One of the most important reasons for using fresnel elements is that they are much thinner than non-fresnel elements which have the same optical characteristics. Space economy is the most important benefit and it derives from the fact that only the useful portion of an optical member is reproduced rather than the entire member.

When the number of prism sections or components is increased materially it becomes practical to use simple wedges acting as prisms instead of forming the large fresnel prism of annular components. This is shown in FIG. 7 and FIG. 7A where the element 300 is formed of annular sections or components such as in the case of the element 218 of FIG. 6B but there are more of such components and the radial dimension becomes less and less as the center is approached. In this case there are annular elements 302, 303, 304, 305, 306, 308, 310, 312, 314 and 316 with the center 318 being cylindrical. The annuli are divided into segments by radial lines such as shown at 320. It is preferred that these segments have a roughly one-to-one aspect ratio, that is, their radial dimension is about the same as their circumferential dimension. In other words, such segments are more or less curvilinear squares whose corner angles are 90°. One such curvilinear square close to the edge is shown at 322 formed of heavy lines for illustrative purposes.

If made from original prisms the master for this structure would require the making of many rings including very thin and small ones and their careful assembly and orientation. This is expensive and difficult. In the structure of FIG. 7, the element 300 is made up of a large number of small wedges which have been assembled together. For example, a prism of the proper dimensions for any given ring is formed as an elongate "stick". The edges are ground off to form the cross section intended for the particular ring, that is, the cross section will have the appearance of the single component 322. The stick is then sliced into as many components as needed, which in this case will be twenty, arranged in a circle and cemented together. Each of the rings can be adjusted to direct transmitted light coming through its rear at suitable forward photoconductors which can be located generally in a circle about the axis of the element 300, but each sector such as 322 may be individually oriented to point to a single location on a television camera tube target or electrode, for example, to give substantially greater resolution of the scattered light.

The aspect ratio which is preferred gives the same amount of so-called smearing in circumferential and radial directions.

An apparatus which is constructed utilizing the element 300 could combine reflecting means such as shown in FIGS. 3, 4 and 5 with the light deviating element to achieve the added advantage of increased radiant energy through gathering both forward and back scattered light.

The invention may be embodied, as shown in FIG. 8, in a system in which the collecting of the scattered radiant energy is effected by reflection and the deviation by reflection as well. Only the basic elements of the system are illustrated in FIG. 8 for simplicity.

The collecting element in the system 400 of FIG. 8 comprises an ellipsoidal reflector 402 whose construction is not significantly different from the reflectors 122 and 122' previously described in detail in connection with FIGS. 3, 4 and 5. It may be assumed to be a vessel containing liquid, with the particles being investigated injected in sheath flow by way of the entrance pipe 404 and carried away by the discharge conduit 406. The optical axis of the system is at 408 and a suitable source of radiant energy such as a laser 410 is disposed to direct its fine beam along the axis 408 into the reflector 402 where it intersects the path of the sample particles at the left hand focal point of the ellipsoidal reflector. This point is identified in the diagram FIG. 8A as f1 and it comprises the sensing zone from which light scattering takes place.

In FIG. 8 there is a small window at 412 through which direct radiant energy emerges to enter the dump 414. The scattered radiant energy is collected and directed forward from the reflector in a cone which has its greatest diameter at the reflector interior defined by the outermost extent thereof and its apex at the second focal point of the ellipsoidal reflector 402. In the practical device, the cone of radiant energy never reaches the focal point, but this point is seen at f2 in the diagram of FIG. 8A. The focal points f1 and f2 and the axis of the cone all lie on the optical axis 408.

A composite reflector assembly is designated generally as 416 and it comprises a series of elliptical mirror rings, here shown as six at 418, 419, 420, 421, 422 and 424 arranged in a particular manner. This will be described presently but for the moment it will be taken that radiant energy can't get past the reflector assembly 416 from left to right in FIG. 8, and only the laser beam from source of radiant energy 410 can pass through the reflector assembly 416 from right to left in FIG. 8 by reason of the center hole 426 in the central elliptical ring 424. The assembly 416 will normally comprise an integral or unitary structure when made commercially and is called a composite mirror in the claims. Such a mirror as 416 will have multiple reflecting surfaces corresponding to the rings 418, 420, 422 and 424 or parts of such rings. The mirror surfaces are all facing to the left as viewed in FIG. 8 so that the radiant energy received against such surfaces is deviated from their direct paths by being reflected or returned toward the ellipsoidal reflector 402 but at different angles to locations laterally thereof.

All of the elliptical reflector ring surfaces 418, 420, 422 and 424 surround the point 428 on the axis 408. All have the same angle of tilt α with respect to the axis, this angle α being chosen to be of such degree that the reflected focal points of all ring surfaces will occur at locations conveniently outside of the ellipsoidal reflector 402 where photodetectors such as 430, 432, 434 and 436 may be positioned. Each ring 418, 420, 422 and 424 is intended to receive a different annular portion of the radiant energy cone projected from left to right in FIG. 8 and each is required to reflect the radiant energy it receives to a different location. In effect, therefore, each ring is required to fold the cone axis to a different circumferential location and cause confluence of the radiant energy it has captured at such location.

To receive an annular portion of radiant energy while being in a disposition tilted relative to the axis 408 each ring surface must be elliptical. To reflect to a different circumferential location, each ring must have an angular position about the axis 408 different from all others while maintaining its angle α and its center 428.

In FIG. 8C the assembly of rings or arcuate mirror surfaces, as they may be called, is viewed along the axis 408 of FIG. 8 looking from left to right. The ellipsoidal reflector 402 and its attendant apparatus is not shown. The locations of the faces of the photocells 430, 432, 434 and 436 are indicated to illustrate the angular disposition around the axis 408 (which is normal to the paper in FIG. 8C) of each elliptical ring. To enable visualizing the angular disposition, each elliptical ring has been marked with a bar in the view lying on its long axis. Thus, the ring 418 has the bar 438, the ring 419 has the bar 439 the ring 420 has the bar 440, the ring 421 has the bar 441 the ring 422 has the bar 442 and the ring 424 has the bar 444. The explanation should be considered while also looking at FIG. 8D which is intended to be an axial end-on view from the left of the reflector 402 in FIG. 8, looking to the right with nothing shown but the reflector outline and the folded back axis of each of the rings.

Starting with the outermost elliptical ring mirror surface 418, its major axis or diameter lying on the bar 438 is chosen to lie in a vertical plane defined by the axis 408 and the major axis or diameter of ring 418. It should be borne in mind that there is still an angle α between the plane of the ring 418 and the axis 408. The axis 408 is therefore folded back toward the reflector 402 and is shown at 408-1 in FIGS. 8 and 8D at an identical angle $\alpha_1$ with axis 408 as a mirror image as indicated in FIG. 8A which shortly will be described. Note that this angle $\alpha_1$ as well as the angle α will not be 90° because of the tilt of the mirror 416. The radiant energy cone captured by the reflective surface of ring 418 may be conceived of as a hollow cone which is entirely folded back, but on the oblique axis 408-1. Its focal point or point of confluence of that portion of radiant energy it has deviated is at the top of the reflector 402 spaced away by a practical distance and the photodetector 432 is located precisely at that point of confluence. This can be optionally an aperture as described above in connection with FIGS. 2D and 2E.

Now consider the next inner elliptical ring 420. It is smaller than the ring 418, is tilted by the same angle α and centered on the same point 428. By examining the location of its bar 440, it is seen that the ring has been rotated about the axis 408 in a counterclockwise direction by the angular extent $\beta_1$ which has been chosen to be about 30° in the view of FIG. 8C. By the same explanation given above, the axis 408 and the portion of the radiant energy cone captured by the reflective surface of the ring 420 has been folded back along the axis 408-2 and comes to a focal point or confluence of radiant energy at the location of the photodetector 430 (shown staggered for convenience in FIG. 8).

The same explanation applies to the ring 422 which has been rotated by the angle $\beta_2$ clockwise from vertical in FIG. 8C and the ring 424 which has been rotated by the angle $\beta_3$ clockwise from vertical. The equivalent folded back axes of deviation for these rings are 408-3 and 408-4 respectively. The focal points of confluence are at the faces of the photodetectors 454 and 436, respectively.

The diagram of FIGS. 8A and 8B may assist in understanding the basis for functioning of the system 400.

The ellipsoid of the elliptical reflector 402 is shown in FIG. 8A by the broken line oval 450. The focal point f1 would be the sensing zone, and all radiant energy collected by the ellipsoidal reflector 402 would focus and confluence at the focal point f2. This is a cone of radiant energy which is, for convenience, shown to be bounded by the lines 452 on the left, with typical interior rays shown at 454 and 456.

A plane mirror 416' has been interjected in the cone 452 at the point 428, tilted at an angle α relative to the axis 408. The projected cone 452 is captured by this mirror 416' and deviated. But for the mirror 416', the cone 452 would continue to project its radiant energy to the right of the mirror 416' along the paths indicated at 452', 454' and 456' to confluence at f2. Due to the mirror 416' the right hand part 452' of the cone 452 is folded back and this is effected along the folded axis 408-F at an angle $α_1$ equal to angle α relative to the plane of the mirror 416' (left side in FIG. 8A) so that the folded part of the cone 452 now has the configuration 452-F and the focus or point of confluence f2 has also been folded back and becomes the point f2-F. The photodetector 432' can now pick up the deviated radiant energy alongside of reflector 402.

If we considered that the cone 452 were made of a number of concentric nested right circular cones, an axial view at any point to the left of the mirror 416' toward reflector 402 would show a series of perfectly annular rings, but their extensions onto the tilted mirror would produce a series of elliptical rings. Since we have chosen to locate the plane mirror 416' normal to the paper, the major axes or diameters of all elliptical rings 418', 420', 422' and 424' are vertical as indicated by the aligned bars 438', 440', 442' and 444'. Because all are in the same plane there is only one folded axis 408-F.

Now if we should cut the rings 418', 420', 422' and 424' from the integral mirror 416' and rotate them about the common axis 408 as explained in connection with FIGS. 8C and 8D, then join them together as an integral composite mirror, the result would be the mirror 416 of FIG. 8. The confluent locations would then be spread circumferentially about the reflector 402 on the axes 408-1, 408-2, 408-3 and 408-4, respectively.

While it may seem that there would be interference physically between rings, it should be remembered that they are ellipses and will not be in the same planes, and even if parts may tend to shadow one another due to some choice of angles, these shadows may be minimized by keeping the angles α and $β_1$, $β_2$ etc small. It is even practical to use portions of rings and adjust the centers slightly along the axis 408 as well as have slightly different angles α for each ring to achieve the most practical alignment of the points of confluence or locations of the photodetectors.

In this manner the photodetectors need not be in a common circle as in FIG. 8C but could be in a straight or arcuate line tangent to the outer circumference of the reflector 402; they could all be on one side or the other or both or on the bottom; they could be spaced evenly around the reflector or axially staggered in any of these locations.

As mentioned above, the use of apertures, or irises can be combined to purify the confluenced radiant energy falling on the respective photodetectors. Likewise, the technique used in achieving the multifacet structure which is described in connection with FIGS. 7 and 7A may be applied to the construction of a mirror in the system 400. The angle of tilt α would be very nearly the same for all facets since the television receiving photodetector would be located at one point, there being only very fine variations.

Figure 8E:
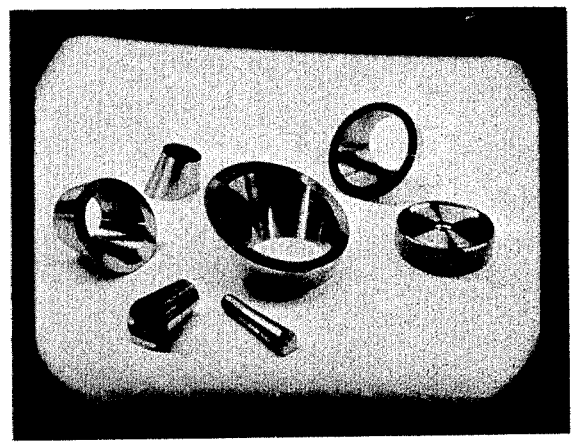
FIGS. 8E, 8F, 8G and 8H are photographic views in perspective of a model constructed to show how the mirror of FIG. 8 is derived.
Figure 8F:
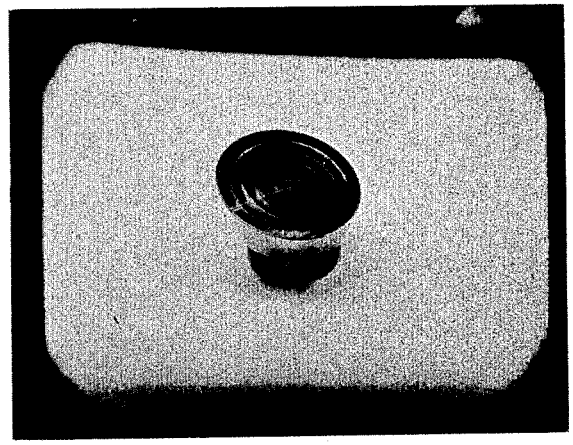

In order to demonstrate the actual construction of the mirror 416 of FIG. 8, a metal model was constructed and photographed in FIGS. 8E, 8F, 8G and 8H. In FIG. 8E there is shown six conical members which are turned in metal and which nest, each member representing a conical beam, the ends being cut off on an angle. The cones would correspond generally to those generated at 452', 454', 456' etc in FIG. 8A. In FIG. 8F, these cones have all been assembled and connected to a base to hold them in assembly so that they could be photographed. Note that a line groove has been cut across each cone face as indicated at 438', 440', 442' and 444' in FIG. 8B. All grooves are aligned in FIG. 8F because the cones have not been rotated. Thus the assembly in FIG. 8F is the equivalent of the rays and mirror 416' of FIG. 8A.

Figure 8G:
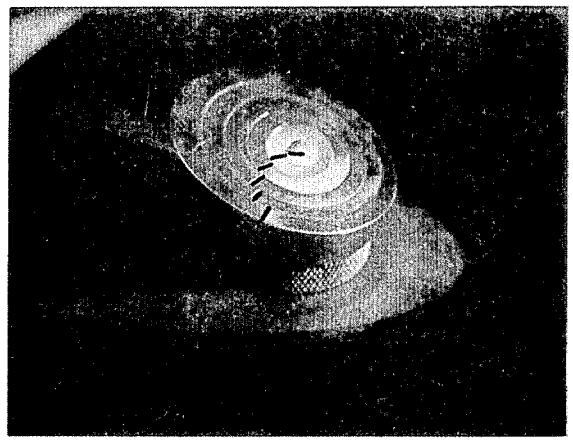
Figure 8H:
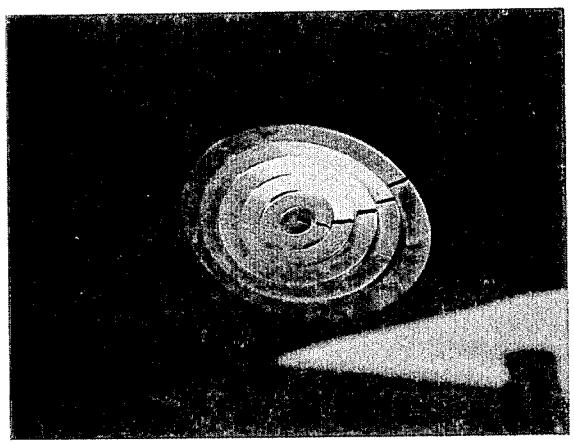

FIGS. 8G and 8H are the equivalent of the rays and mirror 416 of FIG. 8. The shifted grooves are readily seen in each view, having been strengthened by dark lines marked on the photographs.

In the claims, reference to refraction shall be taken to mean a deviation of light or radiant energy by a transmitting element such as a simple or fresnelled assembly of prisms each of which deviates an entrance ray by the same angle as any other ray.

It is seen that the invention is capable of wide variation and flexibility of use both as to the apparatus and the method of using the same, without departing from the spirit or scope of the invention as defined in the appended claims.

What is desired to secure by Letters Patent of the United States is:

1. A method of measuring the directional distribution properties of the radiant energy of a particle for particle identification or the like which comprises:
   A. passing the particle through a sensing zone and illuminating the particle with an incident beam of radiant energy,
   B. collecting at least some of the directionally distributed radiant energy produced by the intersection of the particle and the beam and projecting the same toward a focal point in space remote from the sensing zone,
   C. intercepting the projected portion of radiant energy and deviating the same along a plurality of different paths independently of the collecting,
      i. each path being arranged to comprise the radiant energy gathered from a particular geometric area of the projected portion,
      ii. the geometric areas being different,
      iii. the axis of each path being deviated from extending toward said remote point in space,
      iv. each path serving to cause confluence of the radiant energy of its said path at a particular location,
      v. the locations of the respective confluences of radiant energy being spaced from one another, and
   D. measuring the respective intensities of the radiant energy confluence at the respective locations where confluenced.

2. The method as claimed in claim 1 in which the radiant energy is scattered at the sensing zone.

3. The method as claimed in claim 2 in which primarily the back scattered radiant energy is collected.

4. The method as claimed in claim 2 in which both back scattered and forward scattered radiant energy are collected.

5. The method as claimed in claim 2 in which a portion of the scattered radiant energy is collected and projected by reflection.

6. The method as claimed in claim 5 in which the deviating is effected by reflection.

7. The method as claimed in claim 5 in which the deviating is effected by refraction.

8. The method as claimed in claim 7 in which the stream of liquid is enveloped in another stream of the same liquid to move through the sensing zone in sheath flow.

9. The method as claimed in claim 1 in which a portion of the scattered radiant energy is collected and projected by refraction.

10. The method as claimed in claim 9 in which the deviating is effected by reflection.

11. The method as claimed in claim 9 in which the deviating is effected by refraction.

12. The method as claimed in claim 11 in which the center of said arriving confluence of radiant energy is masked before measurement.

13. The method as claimed in claim 2 in which the focal point in space is chosen to be in alignment with the sensing zone and the axis of the incident beam, and the particle is passed through the sensing zone at a substantial angle relative to said beam axis.

14. The method as claimed in claim 2 in which the incident beam of radiant energy includes energy at a plurality of wave lengths, there being separate paths and locations for each respective wave length at different deviation angles from each geometric area.

15. The method as claimed in claim 2 in which the particle is entrained in a stream of liquid of a particular index of refraction and the sensing zone is immersed in a body of liquid having substantially the same index of refraction.

16. The method as claimed in claim 2 in which each confluence of radiant energy arriving at its respective location is shielded from all other radiant energy at said location to purify the same.

17. The method of making a fresnel element for use in measuring light scattering properties of particles which comprises:
A. forming a disc of segments of prisms, there being a plurality of concentric annuli of said segments, the annuli decreasing in radial dimension toward the axis of the disc,
B. at least each annulus of segments having its projected axis of deviation oriented differently from the orientation of the projected axes of deviation of the other annuli,
C. each of said axes of deviation being spaced from one another at least on a plane normal to the said axis of the disc and symmetrical about said disc at said plane,
D. using said disc as a master to make a mold and molding said fresnel element out of light transmitting material from said mold.

18. The method of making a fresnel element as claimed in claim 17 in which each segment has a projected axis of deviation different from the axes of projection of all other segments, the said axes of deviation of all segments meeting said plane form an area generally of the size of a television camera target capable of being scanned electronically.

19. Apparatus for measuring the directional distribution of radiant energy produced by particles for identification or the like of said particles which comprises:
A. a source of radiant energy arranged to project a beam of radiant energy along a first axis,
B. a sensing zone on said first axis,
C. means for moving particles through said sensing zone to produce scattering of the radiant energy from the beam,
D. means for collecting some of said scattered radiant energy and projecting same toward a focal point in space,
E. means for receiving the collected radiant energy before it reaches the focal point and deviating the same selectively with respect to different geometric portions of the collected energy to generate a plurality of different respective paths having different respective axes and confluence of radiant energy in said respective paths at different respective locations, and
F. means for measuring the intensity of the confluence of radiant energy at each location.

20. The apparatus as claimed in claim 19 in which the deviating means are reflective.

21. The apparatus as claimed in claim 19 in which the deviating means are refractive.

22. Apparatus as claimed in claim 19 in which the collecting means are radiant energy reflective.

23. Apparatus as claimed in claim 22 in which the collecting means comprise a generally ellipsoidal reflector.

24. Apparatus as claimed in claim 22 in which the collecting means comprise an ellipsoidal reflector having the sensing zone at its minor focus.

25. Apparatus as claimed in claim 24 in which said ellipsoidal reflector has a window on its axis adjacent its center, said deviating means being located thereat and comprising a refracting element.

26. Apparatus as claimed in claim 25 in which said ellipsoidal reflector has a second window on its axis at its end adjacent its minor focus and means on the exterior of the reflector to capture and refract distributed radiant energy emerging from said second window.

27. Apparatus as claimed in claim 25 in which the particle moving means include means for entraining said particles in a stream of first liquid, means are provided for filling the reflector with a second liquid having a refractive index similar to that of the first liquid and means are provided for leading at least most of the first liquid out of the reflector after it has passed through the sensing zone.

28. Apparatus as claimed in claim 27 in which means are provided to surround the stream of first liquid with an envelope of third liquid of a similar refractive index under pressure to cause the movement through the sensing zone to be sheath flow.

29. Apparatus as claimed in claim 19 in which the collecting means are radiant energy refractive.

30. Apparatus as claimed in claim 29 in which the collecting means comprise a lens system.

31. Apparatus as claimed in claim 19 in which the collecting means are both radiant energy refractive and radiant energy reflective.

32. Apparatus as claimed in claim 19 in which the particle moving means include means for entraining the particles in a liquid and means for flowing the liquid through the sensing zone.

33. Apparatus as claimed in claim 32 in which the collecting means comprise an ellipsoidal reflector, the sensing zone is at a focal point of the reflector, the reflector is enclosed and has a closure at an otherwise open end thereof which includes said deviating means, said reflector having means for filling the interior thereof with a second liquid of the same refractive index as that in which the particles are entrained and means are provided for leading the first liquid out of the reflector.

34. Apparatus for measuring the scattering of radiant energy produced by particles for identification or the like of said particles which comprises:
A. a source of radiant energy arranged to project a concentrated beam of said radiant energy along a first axis,
B. a sensing zone, said concentrated beam being directed to pass through said sensing zone,
C. means for moving particles in a stream of fluid to flow through said sensing zone at such an angle relative to said first axis and with such dilution in said fluid as to cause scattering of radiant energy by each particle as it passes through said sensing zone,
D. means for collecting at least some of said scattered radiant energy from certain scattering angles about said sensing zone and projecting same as a composite cone of varying intensity considered on a planar frontal aspect, the variations in intensity being related generally to the respective certain scattering angles, said composite cone being projected toward a focussing point in space on said first axis remote from said sensing zone,
E. radiant energy deviating means having a front surface and a rear surface interposed between said collecting means and said point in space and arranged to receive the projected radiant energy composite cone on its rear surface, transmit the same and have the radiant energy emerge from its front surface albeit in a different composition,
F. said radiant energy deviating means including a plurality of deviating components each constructed and arranged to deviate and focus and confluence the radiant energy of respective different geometric portions of the frontal aspect of said composite cone at locations forward of said front surface and lateral of said first axis whereby to produce a plurality of said locations, the locations being spaced apart and each being individual to a different geometric portion, and
G. photoresponsive means at said locations producing a separate signal for each location related respectively to the intensity of radiant energy confluenced at said locations.

35. The apparatus as claimed in claim 34 in which the collecting means are constructed to collect primarily back scattered radiant energy.

36. The apparatus as claimed in claim 34 in which the collecting means are constructed to collect both back scattered and forward scattered radiant energy.

37. The apparatus as claimed in claim 36 in which the annular components are constructed with optical dimensions derived from a common prism.

38. The apparatus as claimed in claim 37 in which the lens is a fresnel lens and the components are integral with one another.

39. The apparatus as claimed in claim 34 in which the collecting means are radiant energy transmissive in character.

40. The apparatus as claimed in claim 34 in which the collecting means are radiant energy reflective in character.

41. The apparatus as claimed in claim 40 in which the collecting means comprise an ellipsoidal reflector, the sensing zone being located at a focal point of said reflector.

42. The apparatus as claimed in claim 34 in which the collecting means include radiant energy reflection and transmission elements.

43. The apparatus as claimed in claim 34 in which the light deviating means comprise a lens and the deviating components are prismatic, each component being positioned to receive, transmit and deviate the radiant energy of a different one of said geometric portions, the angles of deviation being oriented at least circumferentially to space the resulting beam emerging from each component about said first axis to establish the spacing of said locations.

44. The apparatus as claimed in claim 43 in which all of said prismatic deviating components have the same angle of deviation.

45. The apparatus as claimed in claim 43 in which said lens is a fresnel lens and the components are integral with one another.

46. The apparatus as claimed in claim 43 in which the components are annular whereby the geometric portions are circular parts of said composite beam.

47. The apparatus as claimed in claim 43 in which the components include some which are semiannular and others of different geometric configuration.

48. The apparatus as claimed in claim 43 in which the lens is a fresnel lens and the components are integral with one another.

49. The apparatus as claimed in claim 34 in which the particle moving means include means for entraining the particles in a first liquid and means for flowing the first liquid through the sensing zone.

50. The apparatus as claimed in claim 49 in which the sensing zone is in a vessel and said vessel is adapted to be filled with a second liquid whose index of refraction is substantially the same as that of the first liquid.

51. The apparatus as claimed in claim 50 in which means are provided for surrounding the first liquid with a third liquid of refractive index similar to that of the first and second liquids under pressure to cause the movement of the first liquid through the sensing zone to be a sheath flow.

52. The apparatus as claimed in claim 51 in which the vessel has means for leading the first liquid out of the vessel to provide continuous flow thereof.

53. The apparatus as claimed in claim 50 in which the vessel is an ellipsoidal reflector and the collecting means comprise the interior surface of the reflector at least at one end thereof, the sensing zone being located at the focal point of that end, the reflector being open at its optical central portion with a radiant energy transmitting closure covering the opening and the said first mentioned transmitting means disposed at said opening.

54. The apparatus as claimed in claim 53 in which means are provided for leading the first liquid into the vessel on an angle with the optical axis of said ellipsoidal reflector, the said first axis being aligned with said optical axis of the ellipsoidal reflector and the first mentioned transmitting means are coaxial with said optical axis.

55. The apparatus as claimed in claim 54 in which said leading means include means for producing a sheath flow with a third liquid having the same index of refraction as the other liquids.

56. The apparatus as claimed in claim 34 in which said collecting means and transmitting means are located with respect to said sensing zone to collect and transmit primarily back scattered radiation, the said source being disposed on the same side of said sensing zone as said transmitting means.

57. The apparatus as claimed in claim 56 in which in addition to said first mentioned collecting and transmitting means, there are second collecting and transmitting means located with respect to said sensing zone to collect and transmit forward scattered radiation therefrom, deviate some to a second plurality of locations and second photoresponsive means at said second locations for measuring the intensity of radiant energy at said second locations.

58. The apparatus as claimed in claim 57 in which said collecting means is an ellipsoidal reflector with the sensing zone at a focal point of one end thereof, the first collecting means comprising the interior surface of said ellipsoidal reflector, the first transmitting means being spaced from said sensing zone away from said end and the ellipsoidal reflector being open thereat with the first transmitting means over the opening, there being an axial window at the said one end and the second collecting, transmitting, photoresponsive means and locations being outside of the reflector aligned with said window.

59. The apparatus as claimed in claim 56 which includes means for dumping the direct central radiant energy of said concentrated beam.

60. A composite mirror of multiple reflecting surfaces adapted to receive distributed radiant energy from a source that is directing such distributed radiant energy in a conical solid angle generally along an optical axis toward a focal point remote from said source, the mirror adapted to be disposed with its reflecting surfaces facing said source and arranged to reflect and deviate different geometric zones of the distributed radiant energy away from the focal point in different angles relative to said axis and to confluence thereof at respective separate locations where said confluenced portions of radiant energy from said respective zones can be measured.

61. The composite mirror of claim 60 in which the said surfaces are joined in a single structure.

62. The composite mirror of claim 60 wherein at most all of the reflecting surfaces are planar.

63. The composite mirror of claim 60 wherein each of the reflecting surfaces is planar and comprises a generally arcuate segment of a plane mirror tilted relative to said optical axis, at least some of the segments having radii different from one another whereby to deviate the radiant energy from said geometric zones to confluence at different locations.

64. The composite mirror as claimed in claim 63 wherein the arcuate segments are developments of the same planar mirror arranged at a tilt angle relative to said optical axis.

65. The composite mirror as claimed in claim 64 wherein each arcuate segment is a complete ellipsoidal ring and in addition to having a common angle of tilt is centered on a common point along said axis.

66. The composite mirror as claimed in claim 65 in which each segment has an angular disposition about said optical axis different from the others.

67. Apparatus for measuring the scattering of radiant energy produced by particles for identification or the like of said particles which comprises:
A. a source of radiant energy arranged to project a beam of radiant energy along a first axis,
B. a sensing zone on said first axis,
C. means for moving particles through said sensing zone to produce scattering of the radiant energy from the beam,
D. means for collecting some of said scattered radiant energy and projecting same toward a focal point in space and comprising an ellipsoidal reflector, said focal point lying on the optical axis of the reflector, the radiant energy being projected in the form of a conical solid angle whose apex would extend to said focal point,
E. means for receiving the collected radiant energy of said conical solid angle before it reaches said focal point and deviating the same selectively with respect to different geometric portions of the collected energy whereby to cause confluence of radiant energy at different locations, the deviation being a folding back of said projected radiant energy toward said reflector,
F. said locations being adjacent said reflector and
G. means for measuring the intensity of the confluence of radiant energy at each location.

68. The apparatus as claimed in claim 67 in which the means for receiving and deviating comprise a composite mirror of multiple reflecting surfaces adapted to receive distributed radiant energy from a source that is directing such distributed radiant energy in a conical solid angle generally along an optical axis toward a focal point remote from said source, the mirror adapted to be disposed with its reflecting surfaces facing said source and arranged to reflect and deviate different geometric zones of the distributed radiant energy away from the focal point in different angles relative to said axis and to confluence thereof at respective separate locations where said confluenced portions of radiant energy from said respective zones can be measured.

69. The apparatus as claimed in claim 68 in which each of the reflecting surfaces is planar and comprises a generally arcuate segment of a plane mirror tilted relative to said optical axis, at least some of the segments having radii different from one another in order to deviate the radiant energy from said geometric zones to confluence at different locations.

70. The apparatus as claimed in claim 69 in which the arcuate segments are developments of the same planar mirror arranged at a tilt angle relative to said optical axis and each arcuate segment is a complete ellipsoidal ring having a common angle of tilt and is centered on a common point along said optical axis such that each segment has an angular disposition about said optical axis different from the others.

71. A deviator element for use in an apparatus for measuring polar distribution radiant energy, said element being adapted for receiving a composite beam of distributed radiant energy on one surface, transmitting the radiant energy and deviating different portions of the composite beam in different directions and to different locations where the respective deviated beams can be measured, said element being formed of a plurality of prismatic components each having a geometric relation to a specific geometric portion of the composite beam adapted to be received and said components being joined in unitary form, wherein said element is generally circular, about half of the element being formed of semiannular portions of different radial dimension which are coaxial and the other half being formed of wedge shaped segments centered on the center of the circle.

72. A deviator element for use in an apparatus for measuring polar distribution radiant energy, said element being adapted for receiving a composite beam of distributed radiant energy on one surface, transmitting the radiant energy and deviating different portions of the composite beam in different directions and to different locations where the respective deviated beams can be measured, said element being formed of a plurality of prismatic components each having a geometric relation to a specific geometric portion of the composite beam adapted to be received and said components being joined in unitary form, wherein the respective components include a plurality of annuli of different radial dimension arranged coaxially, and wherein the angle of deviation of all components is the same but the axes of the deviated beams are pointed in different directions circumferentially spaced around the central element axis.

73. The element of claim 72 in which the prismatic components are fresnelled.

74. A deviator element for use in an apparatus for measuring polar distribution radiant energy, said element being adapted for receiving a composite beam of distributed radiant energy on one surface, transmitting the radiant energy and deviating different portions of the composite beam in different directions and to different locations where the respective deviated beams can be measured, said element being formed of a plurality of prismatic components each having a geometric relation to a specific geometric portion of the composite beam adapted to be received and said components being joined in unitary form, wherein the prismatic components are annuli of different radial dimension arranged coaxially with the radial width dimension of said respective annuli decreasing from the periphery toward the center.

75. The element of claim 74 in which all the components are dimensionally based upon the same optically dimensioned prism and have the same angle of deviation but are oriented to point the axes of the deviated beams emerging therefrom in different directions circumferentially spaced around the central element axis.

76. The element of claim 74 in which each annulus is formed from a plurality of different wedge-shaped segments arranged side by side circumferentially.

77. The element of claim 76 in which the ratio of radial width dimension to circumferential dimension of the majority of segments in about one to one.

78. The element of claim 76 in which the prismatic components are fresnelled.

79. A deviator element for use in an apparatus for measuring polar distribution radiant energy, said element being adapted for receiving a composite beam of distributed radiant energy on one surface, transmitting the radiant energy and deviating different portions of the composite beam in different directions and to different locations where the respective deviated beams can be measured, said element being formed of a plurality of prismatic components each having a geometric relation to a specific geometric portion to the composite beam adapted to be received and said components being joined in unitary form, wherein the prismatic components are annuli of different radial dimension arranged coaxially with the radial width dimension of said respective annuli decreasing from the periphery toward the center, all the components being dimensionally based upon the same angle of deviation but are oriented to point the axes of the deviated beams emerging therefrom in different directions circumferentially spaced around the central element axis, and wherein each annulus is formed of a plurality of different segments arranged side by side circumferentially.

80. The element of claim 79 in which the aspect ratio of a majority of segments is about one to one.

81. The element of claim 80 in which the prismatic components are fresnelled.

82. Method of making a deviator element for use in measuring radiant energy directional distribution properties of particles which comprises:
A. producing a prism of a given deviation angle,
B. cutting a plurality of mostly cylinders of graduated size from the prism,
C. assembling the cylinders telescopically and orienting each said cylinder by independent rotation thereof so its deviation direction is different from all others,
D. fixing the assembly to form a master; and
E. molding a deviator element from the master out of a radiant energy transmitting material.

83. The method as claimed in claim 82 in which the prism is made out of a radiant energy transmitting material and the orientation is effected by directing radiant energy through the rear of the assembly, rotating the cylinders independently and choosing the orientation of each cylinder by locating its radiant energy concentration location on a plane spaced from the front of the assembly.

84. The method as claimed in claim 82 or 83 wherein said prism is fresnelled.

* * * * *